United States Patent
Bagherinia

(10) Patent No.: US 12,412,245 B2
(45) Date of Patent: Sep. 9, 2025

(54) METHOD AND SYSTEM FOR AXIAL MOTION CORRECTION

(71) Applicant: CARL ZEISS MEDITEC, INC., Dublin, CA (US)

(72) Inventor: Homayoun Bagherinia, Oakland, CA (US)

(73) Assignee: CARL ZEISS MEDITEC, INC., Dublin, CA (US)

(*) Notice: Subject to any disclaimer, the term of this patent is extended or adjusted under 35 U.S.C. 154(b) by 459 days.

(21) Appl. No.: 18/082,448

(22) Filed: Dec. 15, 2022

(65) Prior Publication Data

US 2023/0196525 A1 Jun. 22, 2023

Related U.S. Application Data

(60) Provisional application No. 63/291,246, filed on Dec. 17, 2021.

(51) Int. Cl.
*G06T 5/10* (2006.01)
*A61B 3/00* (2006.01)
(Continued)

(52) U.S. Cl.
CPC ............. *G06T 5/10* (2013.01); *A61B 3/1005* (2013.01); *A61B 3/102* (2013.01); *A61B 3/12* (2013.01);
(Continued)

(58) Field of Classification Search
CPC .... G06T 5/10; G06T 5/50; G06T 7/20; G06T 2207/10101; G06T 2207/30041;
(Continued)

(56) References Cited

U.S. PATENT DOCUMENTS 6,549,801 B1 4/2003 Chen et al.
7,301,644 B2 11/2007 Knighton et al.
(Continued)

FOREIGN PATENT DOCUMENTS

WO 2012059236 5/2012
WO 2016124644 8/2016

OTHER PUBLICATIONS

Hillmann, Dierck & Bonin, Tim & Lührs, Christian & Franke, Gesa & Hagen-Eggert, Martin & Koch, Peter & Hüttmann, Gereon. (2012). Common approach for compensation of axial motion artifacts in swept-source OCT and dispersion in Fourier-domain OCT. Optics Express. 20. 6761-6776. 10.1364/OE.20.006761. (Year: 2012).*

(Continued)

*Primary Examiner* — Chineyere Wills-Burns
*Assistant Examiner* — Lucius Cameron Gree Allen
(74) *Attorney, Agent, or Firm* — SNELL & WILMER L.L.P.

(57) ABSTRACT

A method and system for correcting axial motion in optical coherence tomography (OCT) data is provided. The method includes collecting, by a processor disposed of in an OCT device, a volume scan of an eye; segmenting a first retinal layer within the volume scan; applying an algorithm for periodic pattern removal of OCT data in the first retinal layer by determining a model of a Fourier transform applicable to a segment of the first retinal layer; and removing transform frequencies associated with the OCT data using the model of the Fourier transform; determining a measure of an amount of axial motion in accordance with a difference of an amount of OCT data captured on a surface of the first retinal layer before and after application of the algorithm for periodic pattern removal; and correcting, the amount of axial motion in the OCT data of the first retinal layer.

14 Claims, 13 Drawing Sheets

(5 of 13 Drawing Sheet(s) Filed in Color)

(51) Int. Cl.
*A61B 3/10* (2006.01)
*A61B 3/12* (2006.01)
*G06T 5/50* (2006.01)
*G06T 5/70* (2024.01)
*G06T 7/20* (2017.01)

(52) U.S. Cl.
CPC .................. *G06T 5/50* (2013.01); *G06T 7/20* (2013.01); *G06T 2207/10101* (2013.01); *G06T 2207/30041* (2013.01)

(58) Field of Classification Search
CPC ............. G06T 5/70; G06T 2207/10024; G06T 2207/10048; G06T 2207/20056; G06T 2207/20201; A61B 3/1005; A61B 3/102; A61B 3/12; A61B 3/0025
USPC ........................................................ 382/131
See application file for complete search history.

(56) References Cited

U.S. PATENT DOCUMENTS

| | | | |
|---|---|---|---|
| 9,332,902 | B2 | 5/2016 | Tumlinson et al. |
| 9,414,065 | B2* | 8/2016 | Moriyoshi ........... H04N 19/513 |
| 9,456,746 | B2 | 10/2016 | Bublitz et al. |
| 10,952,603 | B2 | 3/2021 | Bagherinia |
| 2005/0171438 | A1 | 8/2005 | Chen et al. |
| 2007/0291277 | A1 | 12/2007 | Everett et al. |
| 2010/0027857 | A1 | 2/2010 | Wang |
| 2012/0249956 | A1 | 10/2012 | Narasimha-Iyer et al. |
| 2012/0277579 | A1 | 11/2012 | Sharma et al. |
| 2012/0307014 | A1 | 12/2012 | Wang |
| 2013/0100456 | A1 | 4/2013 | Yu et al. |
| 2013/0163003 | A1 | 6/2013 | Massow et al. |
| 2014/0268038 | A1 | 9/2014 | Schmoll |
| 2015/0131050 | A1 | 5/2015 | Bublitz et al. |
| 2016/0000320 | A1 | 1/2016 | Sharma et al. |
| 2016/0166144 | A1 | 6/2016 | Izatt et al. |
| 2018/0014725 | A1* | 1/2018 | Bagherinia ............. G06T 7/215 |
| 2022/0142471 | A1* | 5/2022 | Ashok .................... A61B 3/102 |

OTHER PUBLICATIONS

Clara Pfäffle, Hendrik Spahr, Dierck Hillmann, Helge Sudkamp, Gesa Franke, Peter Koch, and Gereon Hüttmann, "Reduction of frame rate in full-field swept-source optical coherence tomography by numerical motion correction [Invited]," Biomed. Opt. Express 8, 1499-1511 (Year: 2017).*
Kraus, M. F. et al., "Motion correction in optical coherence tomography volumes on a per A-scan basis using orthogonal scan patterns." Biomedical Optics Express. Jun. 2012. vol. 3, No. 6. p. 1182. Optical Society of America.
Danielson, B.L. et al., "Absolute optical ranging using low coherence interferometry," Applied Optics, vol. 30. No. 21. p. 2975-2979, Jul. 1991.
Hariri, S. et al., "Limiting factors to the OCT axial resolution for in-vivo imaging of human and rodent retina in the 1060nm wavelength range," Optical Express, vol. 17. No. 26, p. 24304-24316. Mar. 2009 Optical Society of America.
Van Den Berg, T.J. et al., "Near infrared light absorption in the human eye media," Vision Res. vol. 37 No. 2, p. 249-253, 1997. Elsevier Science Ltd.
Coello, Y. et al., "Group-velocity dispersion measurements of water, seawater, and ocular components using multiphoton intrapulse interference phase scan," Applied. Optics., vol. 46 No. 35. p. 8394-8401. 2007 Optical Society of America.
Drexler, W. et al., "State-of-the-art retinal optical coherence tomography," Science Direct. Progress in Retinal Eye Research vol. 27 p. 45-88. 2008 Elsevier Ltd.
Drexler, W. et al., "In vivo ultrahigh-resolution optical coherence tomography," Optics Letter vol. No. 1724, p. 1221-1223, 1999 Optical Society of America.

Potsaid, B. et al., "Ultrahigh speed spectral / Fourier domain OCT ophthalmic imaging at 70,000 to 312,500 axial scans per second," Optical Express vol. 16, No. 19. p. 5149-15169. 2008 Optical Society of America.
Povazay, B. et al., "Enhanced visualization of choroidal vessels using ultrahigh resolution ophthalmic OCT at 1050 nm," Optical Express vol. 11, No. 17. p. 1980-1986. 2003 Optical Society of America.
Unterhuber, A. et al., "In vivo retinal optical coherence tomography at 1040 nm-enhanced penetration into the choroid," Optical Express vol. 13 No. 9. p. 3252-3258. 2005 Optical Society of America.
Yasuno, Y. et al., "In vivo high-contrast imaging of deep posterior eye by 1-μm swept source optical coherence tomography and scattering optical coherence angiography," Optical Express vol. 15, No. 10. p. 6121-6139. 2007 Optical Society of America.
Hillman, T. et al., "The effect of water dispersion and absorption on axial resolution in ultrahigh resolution optical coherence tomography," Optical Express, vol. 13 No. 6. p. 1860-1874, 2005 Optical Society of America.
Wolbarsht, M. L. et al., "Melanin, a unique biological absorber," Applied Optics vol. 20, No. 13. p. 2184-2186, 1981 Optical Society of America.
Wang, Y., "Optimal wavelength for ultrahighresolution optical coherence tomography," Optical Express vol. 11, No. 12. p. 1411-1417, 2003 Optical Society of America.
Klein, T. et al., "Megahertz OCT for ultrawide-field retinal imaging with a 1050 nm Fourier domain mode-locked laser," Optical Express vol. 19, No. 4. p. 3044-3062. 2011 Optical Society of America.
Huber, R. et al., "Fourier domain mode locking at 1050 nm for ultrahigh-speed optical coherence tomography of the human retina at 236,000 axial scans per second," Optical Letter vol. 32, No. 14. p. 2049-2051. 2007 Optical Society of America.
Kuznetsov, M. et al., "Compact ultrafast reflective Fabry-Perot tunable lasers for oct imaging applications," Proceedings of SPIE 7554, Optical Coherence Tomography and Coherence Domain Optical Methods in Biomedicine XIV75541F. US 2010 SPIE BiOS. doi:10.1117/12.842567.
Marschall, S. et al., "Fourier domain mode-locked swept source at 1050 nm based on a tapered amplifier," Optical Express vol. 18, No. 15. p. 15820-15831. 2010 Optical Society of America.
Marschall, S. et al., "Broadband Fourier domain mode-locked laser for optical coherence tomography at 1060 nm," Proceedings of SPIE 8213, Proceedings vol. 8213, Optical Coherence Tomography and Coherence Domain Optical Methods in Biomedicine XVI; 82130R. 2012 https://doi.org/10.1117/12.906148.
Hillmann, D. et al., "Holoscopy—holographic optical coherence tomography" Optics Letters vol. 36, No. 13. p. 2390. 2011 Optical Society of America.
Nakamura, Y. et al., "High-Speed three dimensional human retinal imaging by line field spectral domain optical coherence tomography" Optics Express vol. 15, No. 12 p. 7103. 2007 Optical Society of America.
Blazkiewicz et al., "Signal-to-noise ratio study of full-field Fourier-domain optical coherence tomography," Applied Optics. vol. 44, No. 36. p. 7722. 2005 Optical Society of America.
Marschall, S., "Investigation of the impact of water absorption on retinal OCT imaging in the 1060 nm range," Biomed. Opical Express vol. 3, No. 7. p. 1620-1631, 2012 Optical Society of America.
Palmer, K. F. et al., "Optical properties of water in the near infrared," Journal of Optical Society of America, vol. 64, No. 8. p. 1107-1110, 1974.
Lee, Song-Won, "Optimization for Axial Resolution, Depth Range, and Sensitivity of Spectral Domain Optical Coherence Tomography at 1.3 μm", J Korean Phys Soc., vol. 55, No. 6. p. 2354-2360, 2009. doi:10.3938/jkps.55.2354. NIH Public Access.
Godenschweger, F. et al., "Motion correction in MRI of the brain," Phys Med Biol. Mar. 7, 2016. vol. 61, No. 5. p. R32-R56. doi:10.1088/0031-9155/61/5/R32. HHS Public Access.

* cited by examiner

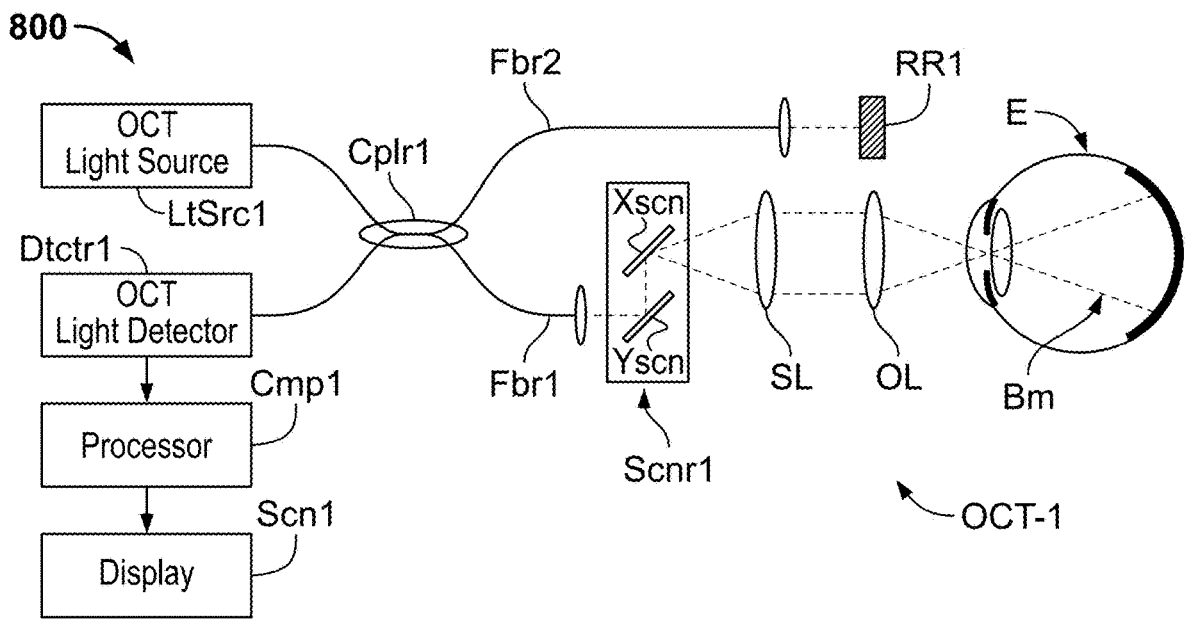
FIG. 8
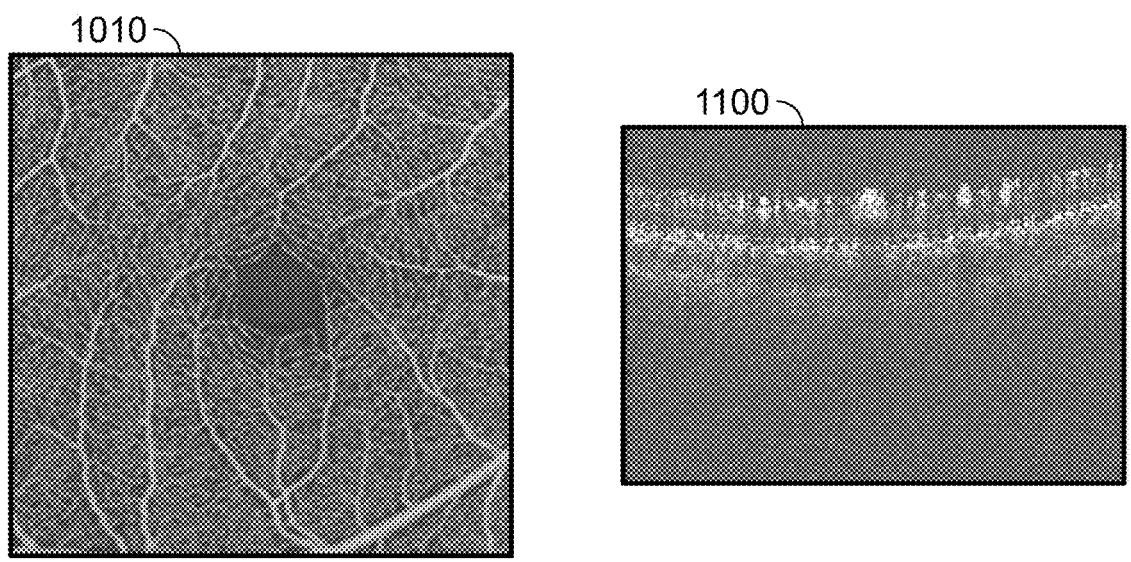
FIG. 10
FIG. 11

METHOD AND SYSTEM FOR AXIAL MOTION CORRECTION

CROSS-REFERENCE TO RELATED APPLICATIONS

This application claims the benefit of priority under 35 U.S.C. 120 to U.S. Provisional Application Ser. No. 63/291,246 entitled "METHODS FOR AXIAL MOTION CORRECTION", filed on Dec. 17, 2021, the entire contents of which are incorporated by reference for all purposes.

FIELD OF INVENTION

The present invention is generally directed to optical coherence tomography (OCT). More specifically, it is directed to techniques for axial motion correction of OCT data with both periodic and non-periodic motion.

BACKGROUND

Optical coherence tomography (OCT) is a non-invasive imaging technique that uses light waves to penetrate tissue and produce image information at different depths within the tissue, such as an eye. An OCT system is an interferometric imaging system based on detecting the interference of a reference beam and backscattered light from a sample illuminated by an OCT beam. Each scattering profile in the depth direction (e.g., z-axis or axial direction) may be reconstructed individually into an axial scan, or A-scan. Cross-sectional slice images (e.g., two-dimensional (2D) bifurcating scans, or B-scans) may be built up from multiple (adjacent) A-scans acquired as the OCT beam is scanned/moved along a fast scan direction, e.g., the X-axis. A volume scan/image (e.g., 3D cube scans, or C-scans) may be constructed from multiple (adjacent) B-scans acquired as the OCT beam is scanned through a set of transverse (e.g., X-axis and/or Y-axis) locations on the sample. For example, when a first B-scan reaches the end of its fast scan (e.g., along the X-axis direction), the beam typically undergoes a fly-back operation (by use of a galvanometer, or galvo) to the starting position offset in the Y-direction in preparation for the next B-scan in the volume/cube scan operation. This results in a raster scan (volume/cube scan) with the X-axis typically characterized as the fast scan direction and the Y-axis characterized as the slow-scan direction.

A difficulty with obtaining OCT scans of the eye is that the eye may undergo motion, both translational (e.g., in the X-Y axis/direction) and axial (e.g., in the Z axis/direction) motion, which can complicate the analysis of the collected data. Uncorrected motion errors can result in jagged and broken images and can complicate the use of automated data analysis algorithms. For example, axial motion correction (AMC) is essential for OCT image analysis such as retinal multilayer segmentation (MLS). Using orthogonal retrace scans is an effective technique for AMC, but sometimes it suffers from axial bulk motion and low image contrast when the retrace scans cross the ONH or large vessels.

Therefore, some sort of motion correction is desirable. In particular, Z-motion correction (e.g., positive and negative motion correction along the Z-axis) can be complicated due to it resulting not only from the movement of a patient's head but also resulting from systemic, internal body operations, such as muscular, peristaltic, cardiovascular, respiratory operations, as well as mechanical vibration in the OCT instrument.

It is at least an object of the present invention to provide Z-motion correction that addresses both axial shift and shear (tilt) error.

It is at least another object of the present invention to compensate for periodic motion in the Z-direction and to use this information for improved retinal boundary layer fit operations.

SUMMARY OF INVENTION

In various embodiments, a method for correcting axial motion in optical coherence tomography (OCT) data is provided. The method includes collecting, by a processor disposed of in an OCT device, a volume scan of an eye; segmenting, by the processor, a first retinal layer within the volume scan; applying, by the processor, an algorithm for periodic pattern removal of OCT data in the first retinal layer by: determining a model of a Fourier transform applicable to a segment of the first retinal layer; and removing one or more transform frequencies associated with the OCT data using the model of the Fourier transform for the periodic pattern removal while leaving unchanged other frequencies associated with OCT data in the first retinal layer; determining, by the processor, a measure of an amount of axial motion in accordance with a difference of an amount of OCT data captured on a surface of the first retinal layer before and after application of the algorithm for periodic pattern removal; and correcting, by the processor, the amount of axial motion in the OCT data of the first retinal layer.

In various exemplary embodiments, the periodic pattern removal further comprises recovering by the processor of a motion-corrected version of the first retinal layer by applying an inverse Fourier transfer after the removal of the frequencies associated with the periodic pattern removal.

In various exemplary embodiments, the method further includes correcting, by the processor, the amount of axial motion, in a second retinal layer.

In various exemplary embodiments, the first retina layer includes an internal limiting membrane (ILM) layer, and the second retinal layer comprises retinal pigment epithelium (RPE) layer.

In various exemplary embodiments, the method further includes defining, by the processor, a retinal thickness map in accordance with a difference in the amount of OCT data contained on the surface of the ILM layer and the RPE layer after the application of an axial motion correction to the ILM layer and the RPE layer.

In various exemplary embodiments, the model for periodic pattern removal is determined by an integral number of oscillations across the Fourier transform.

In various exemplary embodiments, the first retinal layer at least comprises a two-dimensional retinal layer.

In various exemplary embodiments, a method for correcting axial motion in an optical coherence tomography (OCT) C-scan is provided. The method includes collecting, via a first scan direction by a processor disposed of in an OCT device, the first set of scans comprising at least one pair of reference scans from a plurality of reference scans; collecting, via a second direction by the processor, the second set of scans comprising at least one C-scan wherein the at least one C-scan further comprises a plurality of B-scans wherein the second scan direction is orthogonal to the first scan direction; selecting, by the processor, the at least one pair of reference scans from the plurality of reference scans for use in is selecting a set of B-scans that comprise the at least one C-scan; and correcting, by the processor, an amount of axial motion in the set of B-scans by comparison of at least one pair of reference scans.

In various exemplary embodiments, the selection of at least one pair of reference scans includes: determining, by the processor, a measure of the amount of axial motion for the set of B-scans that is based on a separate achievability associated with a single reference scan of the pair of reference scans; and determining, by the processor, a pair of reference scans that meets a preferred measure of axial correction for defining a single pair of reference scans as a dynamic selection.

In various exemplary embodiments, at least one pair of reference scans includes an N number of pairs of reference scans, wherein the N number of pairs of reference scans is determined by the processor using a formula of $2^{N-1}$.

In various exemplary embodiments, the single pair of reference scans include a plurality of A-scans that are collected by the processor in the first scan direction, wherein the set of B-scans comprises the plurality of A-scans that are collected by the processor in the second direction.

In various exemplary embodiments, the method further includes modeling, by the processor, a single pair of A-scans in accordance with a function of a space A(x,y) that defines a lateral position of at least one A-scan contained in the C-scans.

In various exemplary embodiments, the space A(x, y) includes a d-dimensional vector of intensities that are equally spaced in an axial direction (z), wherein at least one A-scan is defined by the space $A_r(x_r, y_r)$ at a lateral position r with coordinates $(x_r, y_r)$.

In various exemplary embodiments, the method further includes determining, by the processor, the selection of at least one pair of reference scans by normalizing a cross-correlation function $\gamma$ between A(x, y) and $A_r(x_r, y_r)$ to determine a corresponding A(x, y) of a current B-scan in a plurality of pairs of reference scans.

In various exemplary embodiments, the method further includes applying, by the processor, using a formula $$\hat{z} = \max\left(\underset{z}{\mathrm{argmax}}\left(\max_{x,y}(\gamma(A(x, y), A_r(x_r, y_r), z))\right)\right)$$

to determine the corresponding A(x, y) of the current B-scan in a plurality of pairs of reference scans wherein a relative shift between $A_r(x_r, y_r)$ and $A(\hat{x}, \hat{t})$ represents an axial shift $\hat{z}$ for a single reference scan.

In various exemplary embodiments, a system for correcting axial motion error in optical coherence tomography (OCT) data is provided. The system includes an OCT device configured to collect a volume scan of an eye; and a processor disposed of in the OCT device configured to: apply an algorithm for periodic pattern removal of OCT data in a first retinal layer to determine a model of a Fourier transform applicable to a segment of the first retinal layer; and remove one or more transform frequencies associated with the OCT data using the model of the Fourier transform for the periodic pattern removal while leaving unchanged other frequencies associated with OCT data in the first retinal layer; determine a measure of an amount of axial motion in accordance with a difference of an amount of OCT data captured on a surface of the first retinal layer before and after application of the algorithm for periodic pattern removal; and correct the amount of axial motion in the OCT data of the first retinal layer.

In various exemplary embodiments, the processor is configured to: correct the amount of axial motion in a second retinal layer.

In various exemplary embodiments, the first retinal layer is positioned higher than the second retinal layer within the retina of the eye.

In various exemplary embodiments, the first retinal layer comprises an internal limiting membrane (ILM) layer, and the second retinal layer comprises a retinal pigment epithelium (RPE) layer.

In various exemplary embodiments, the processor is configured to define a retinal thickness map in accordance with a difference in the amount of OCT data contained on the surface of the ILM layer and the RPE layer after the application of an axial motion correction to the ILM layer and the RPE layer.

In various exemplary embodiments, the model for periodic pattern removal is determined by an integral number of oscillations across the Fourier transform.

In various exemplary embodiments, the first retinal layer at least includes a two-dimensional retinal layer.

The embodiments disclosed herein are only examples, and the scope of this disclosure is not limited to them. Any embodiment feature mentioned in one claim category, e.g., system, can be claimed in another claim category, e.g., method, as well. The dependencies or references back in the attached claims are chosen for formal reasons only. However, any subject matter resulting from a deliberate reference back to any previous claims can be claimed as well, so that any combination of claims and the features thereof are disclosed and can be claimed regardless of the dependencies chosen in the attached claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The subject matter of the present disclosure is particularly pointed out and distinctly claimed in the concluding portion of the specification. A more complete understanding of the present disclosure, however, may best be obtained by referring to the following detailed description and claims in connection with the following drawings. While the drawings illustrate various embodiments employing the principles described herein, the drawings do not limit the scope of the claims.

In the drawings wherein like reference symbols/characters refer to like parts:

Figure 1A:
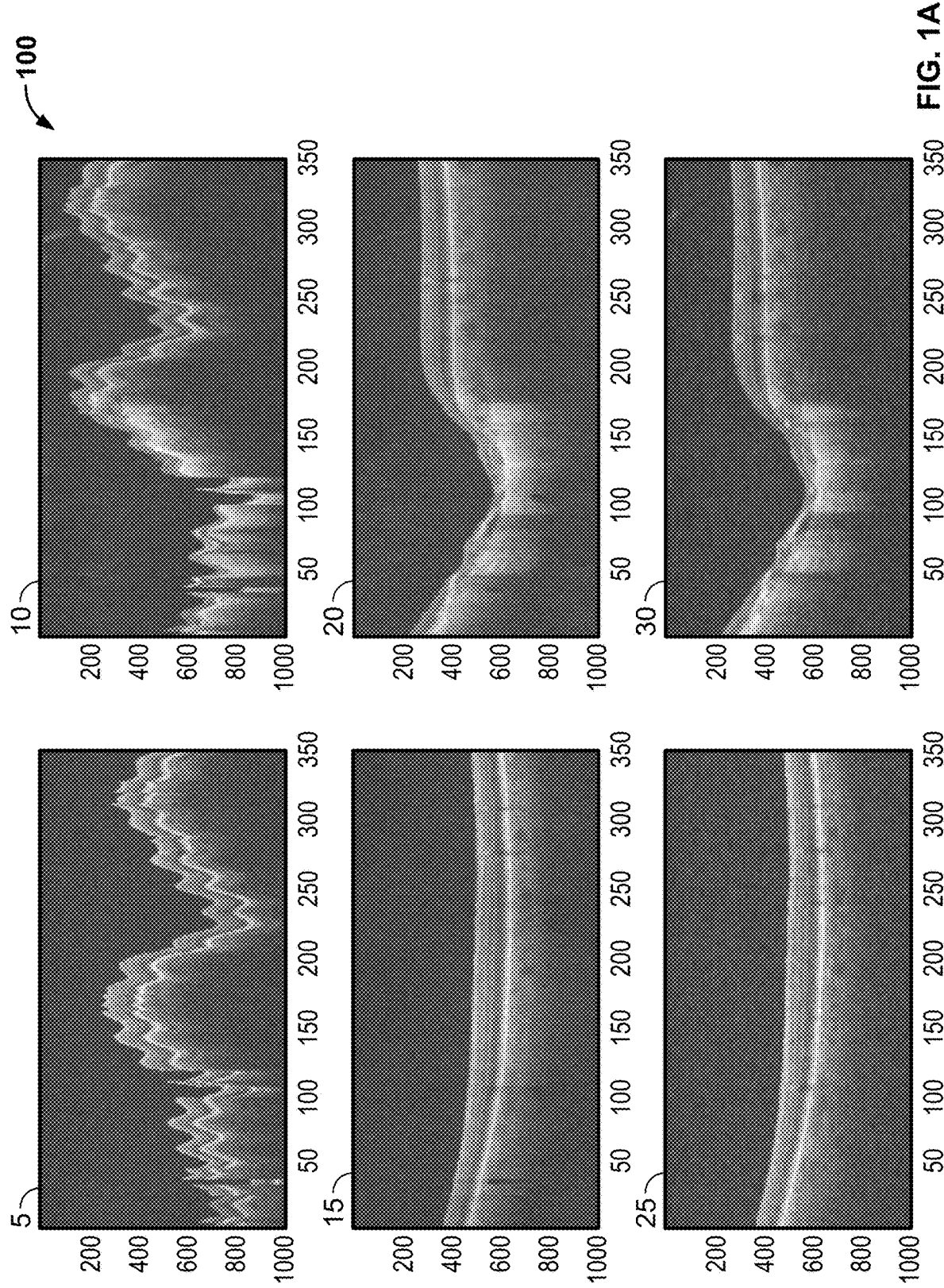
Figure 1B:
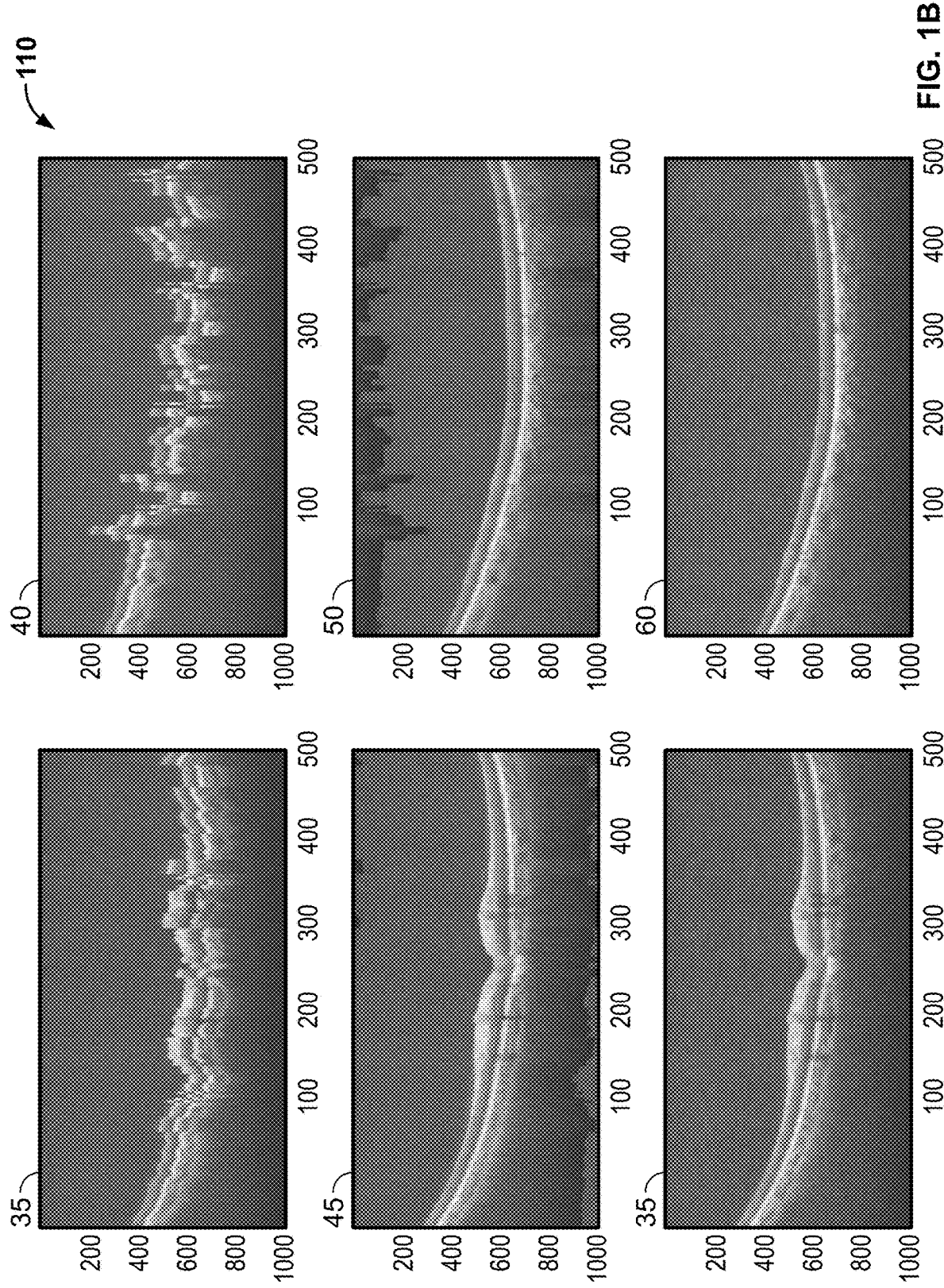
Figure 1C:
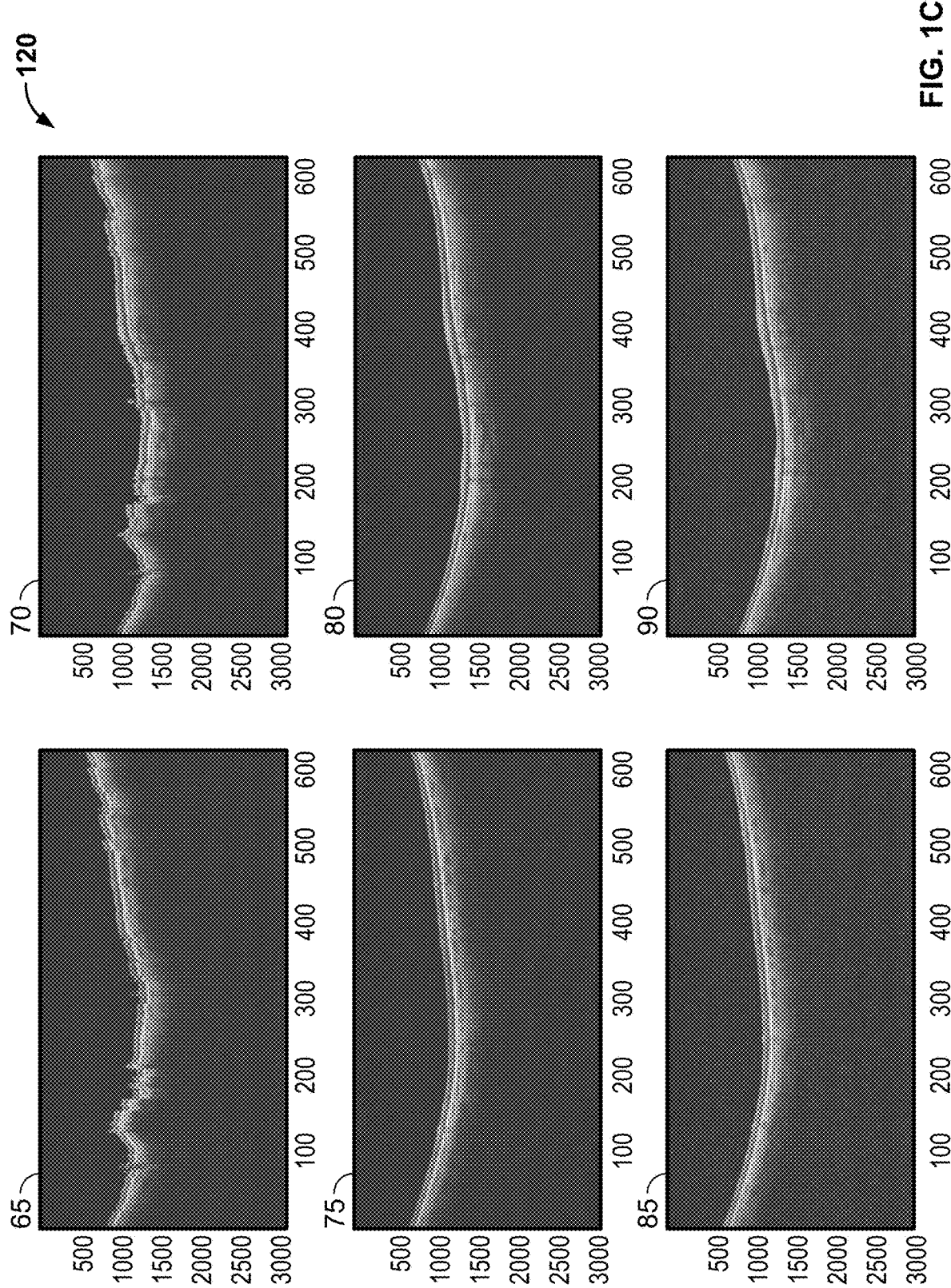

FIGS. 1A, 1B, and 1C illustrate a set of three scans that comprise field-of-views (FOVs) of 6×6 mm, 12×12 mm, and 15×15 mm, respectively, before and after Z-motion correction in accordance with various embodiments.

Figure 2A:
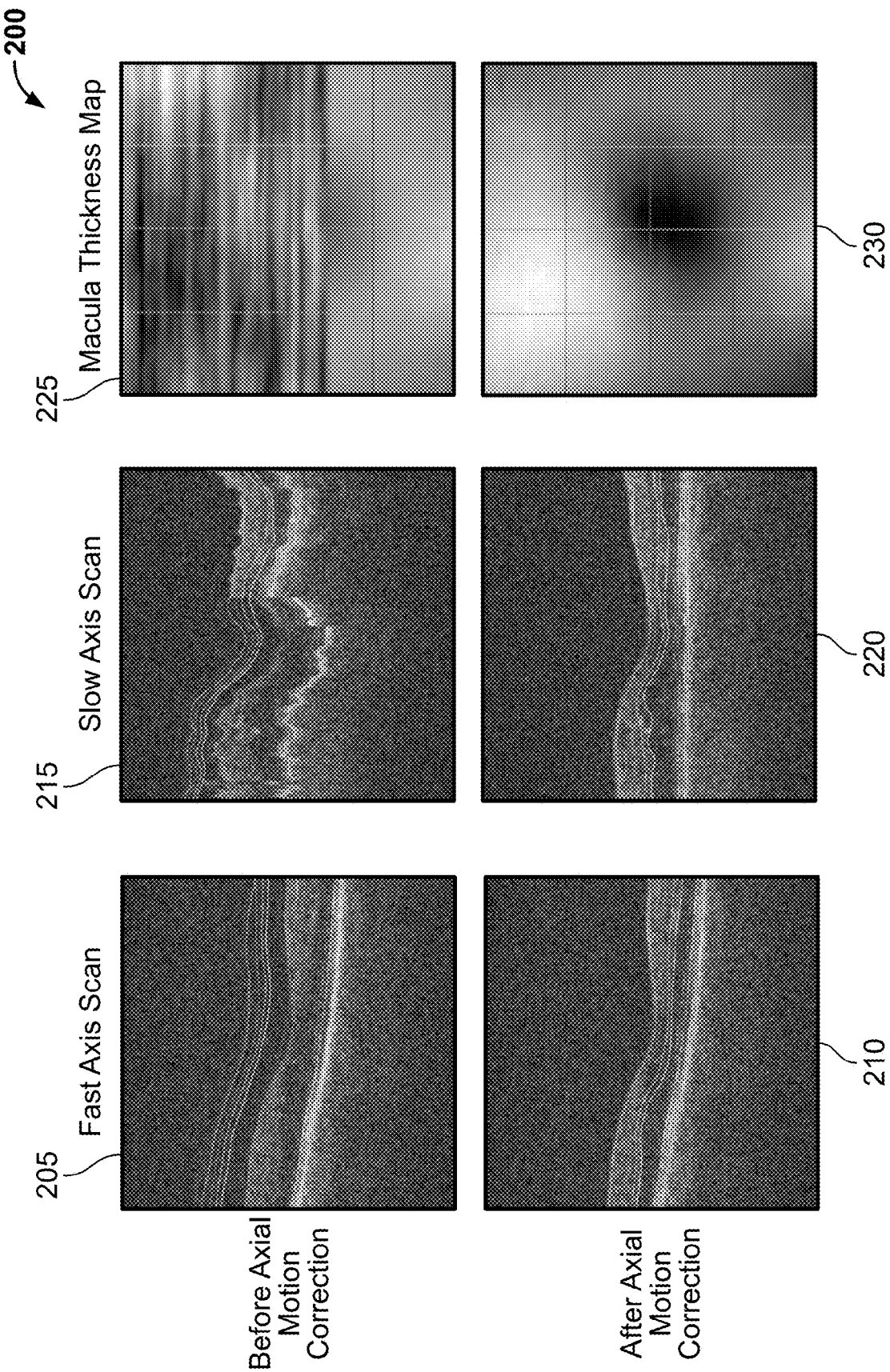
Figure 2B:
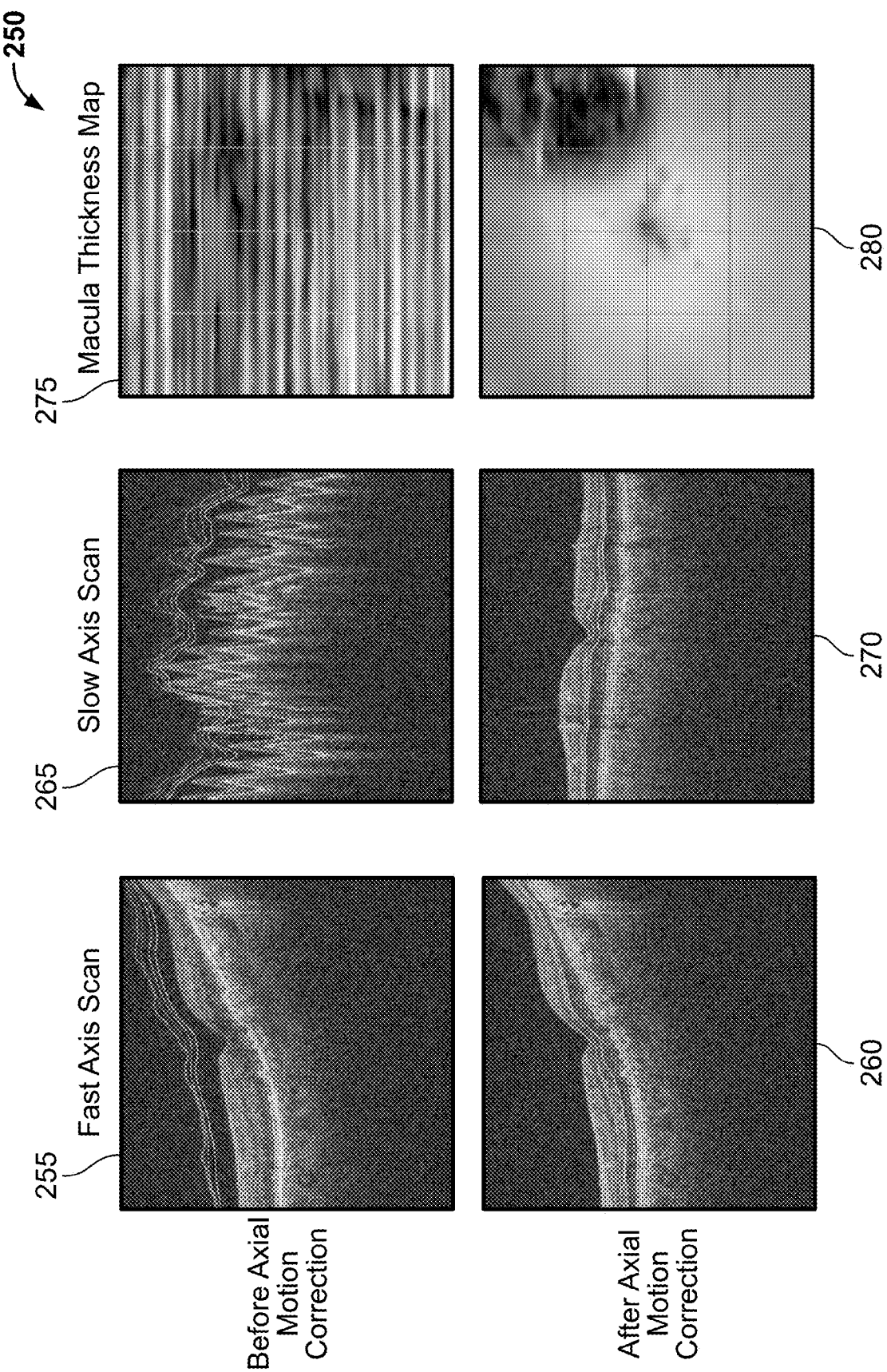

FIGS. 2A and 2B illustrate a set of example scans of the MLS performance before and after axial motion correction is applied in accordance with various embodiments.

Figure 3:
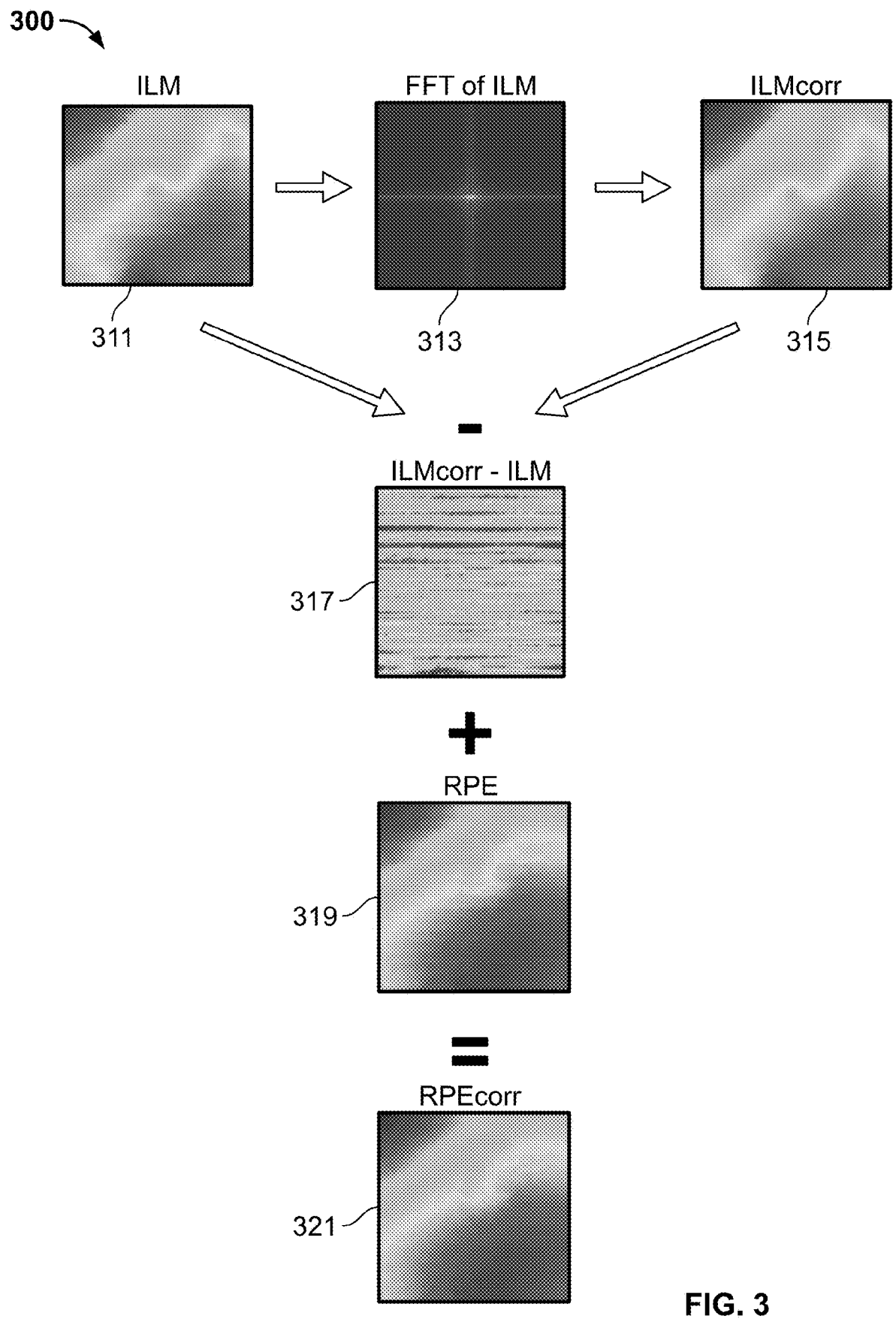

FIG. 3 illustrates a flowchart (process flow) of the present method for periodic axial motion correction in accordance with various embodiments.

Figure 4:
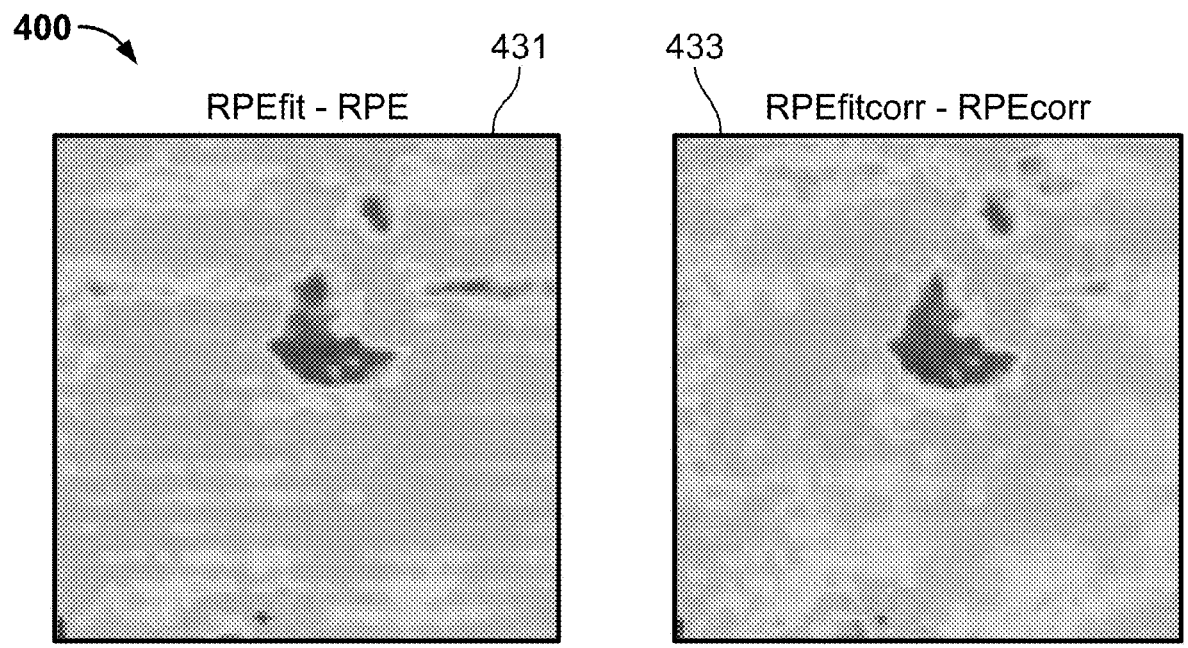

FIG. 4 illustrates a set of exemplary images of the difference between RPE fit and RPE before and after axial motion correction is applied in accordance with various embodiments.

Figure 5:
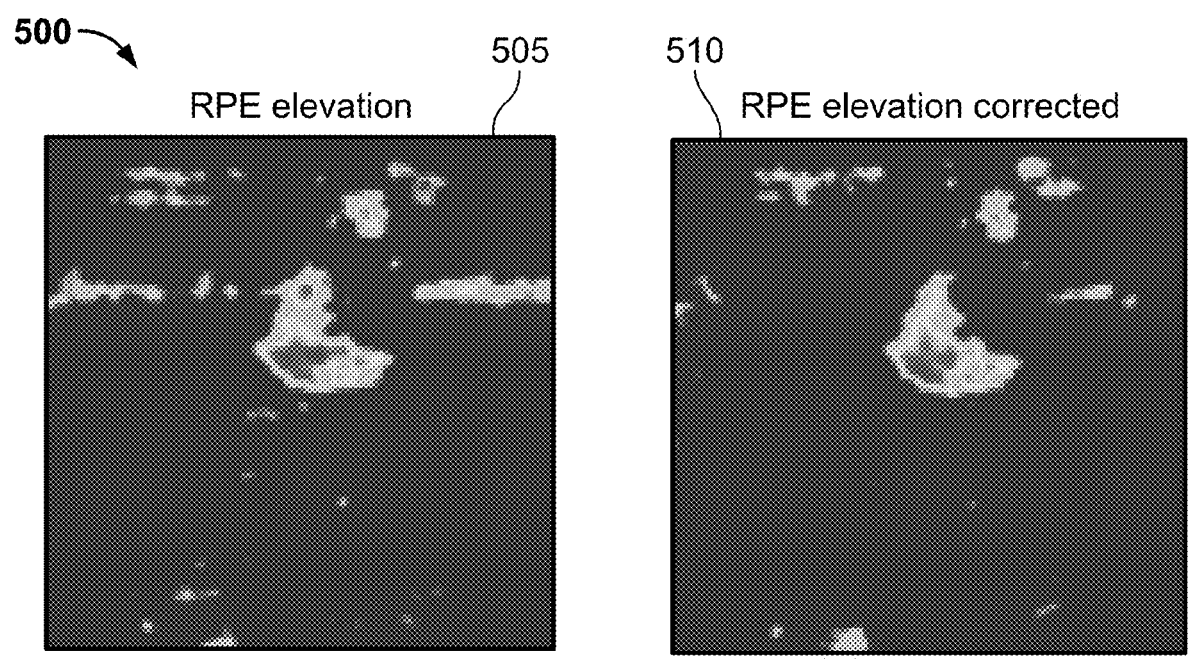

FIG. 5 illustrates a set of exemplary images of the RPE elevation map generated by setting any value smaller than 20 microns (or other suitable numbers, or normalized values) to zero in accordance with various embodiments.

Figures 6A, 6B:
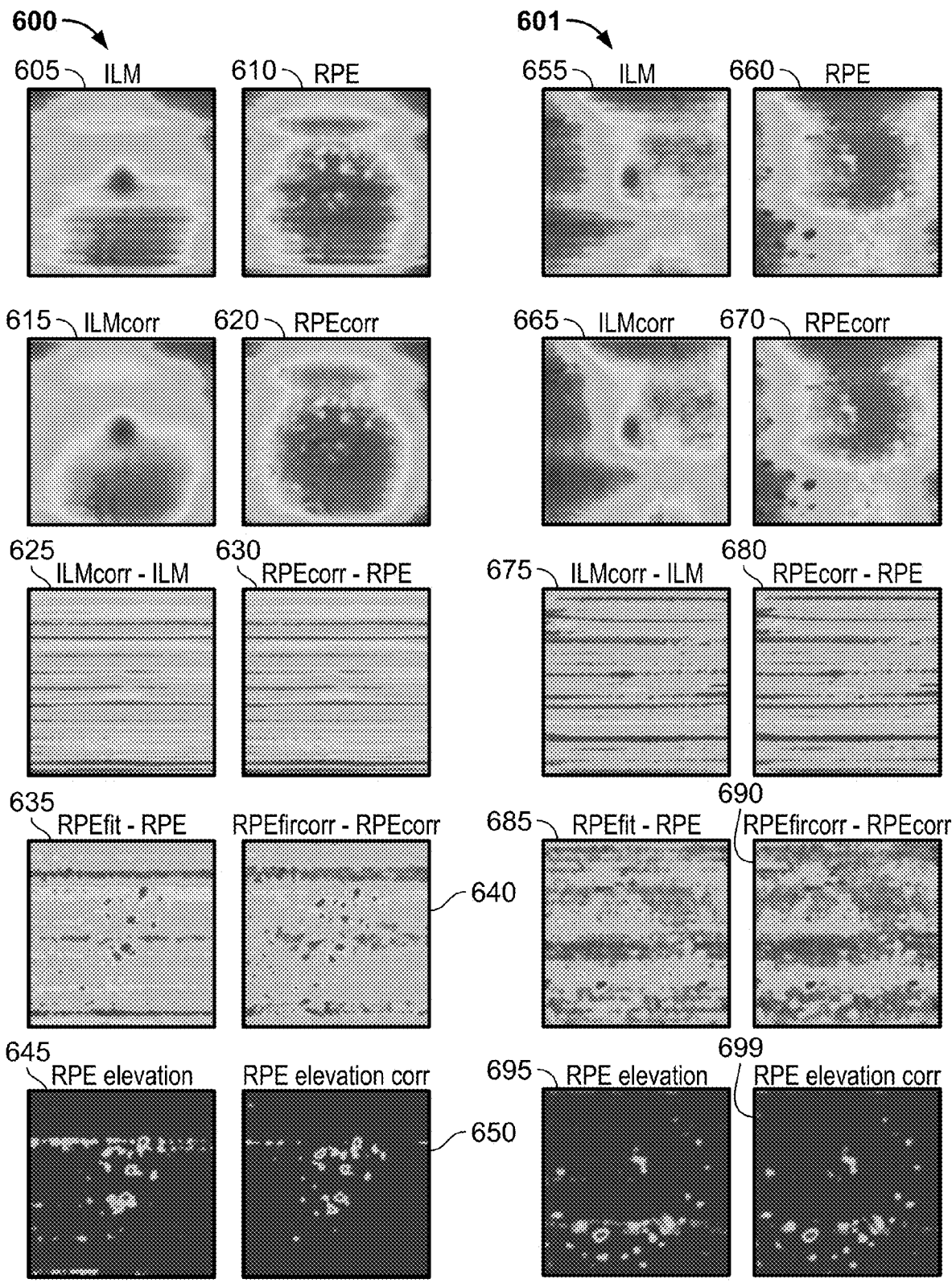

FIGS. 6A and 6B illustrate sets of multiple images that provide additional examples of periodic artifacts, with and without correction in accordance with various embodiments.

Figure 7:
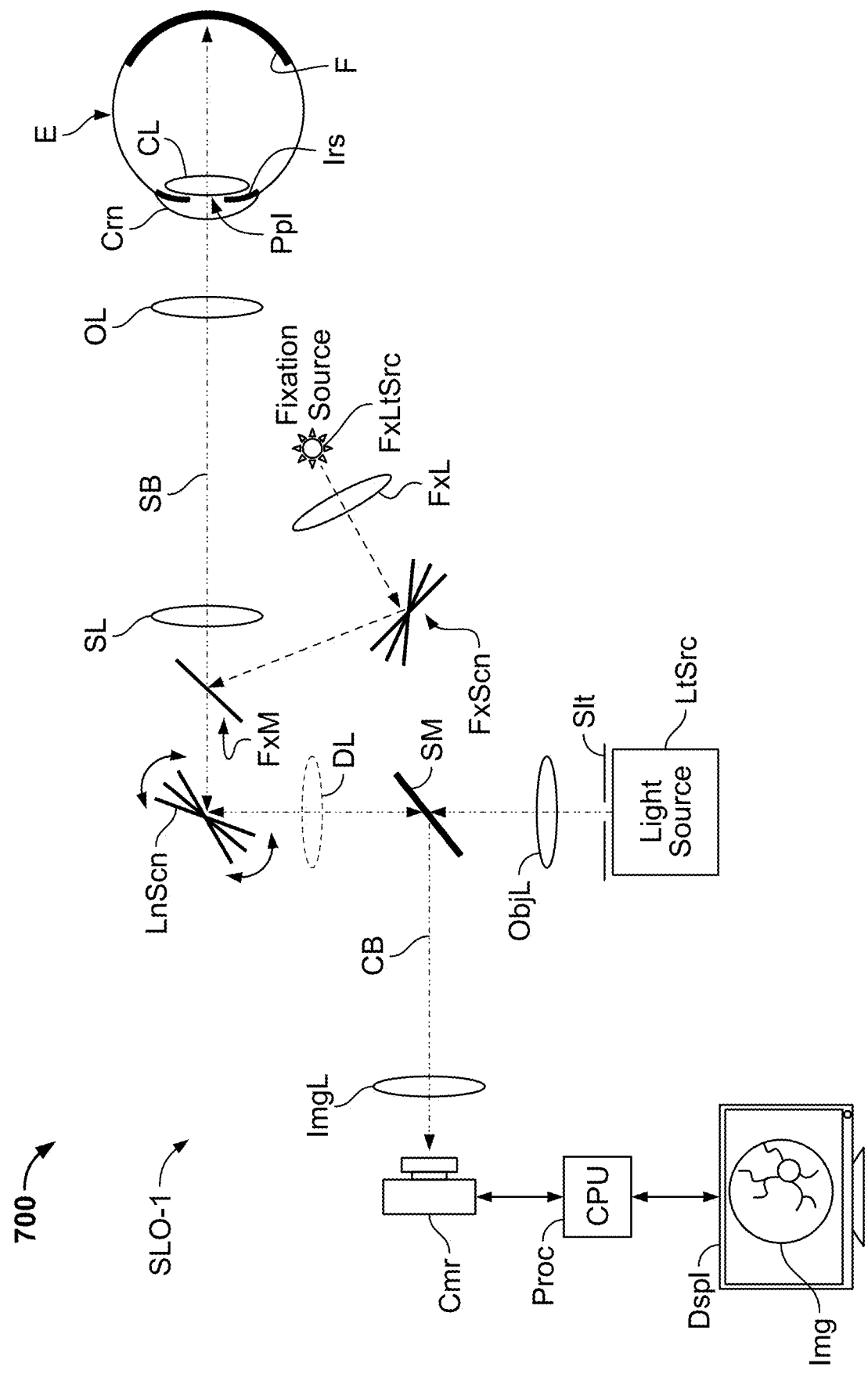

FIG. 7 illustrates a diagram of an exemplary slit scanning ophthalmic system for imaging a fundus in accordance with various embodiments.

FIG. 8 illustrates a diagram of an exemplary frequency domain optical coherence tomography system used to collect 3D image data of the eye that is suitable for use in accordance with various embodiments.

Figure 9:
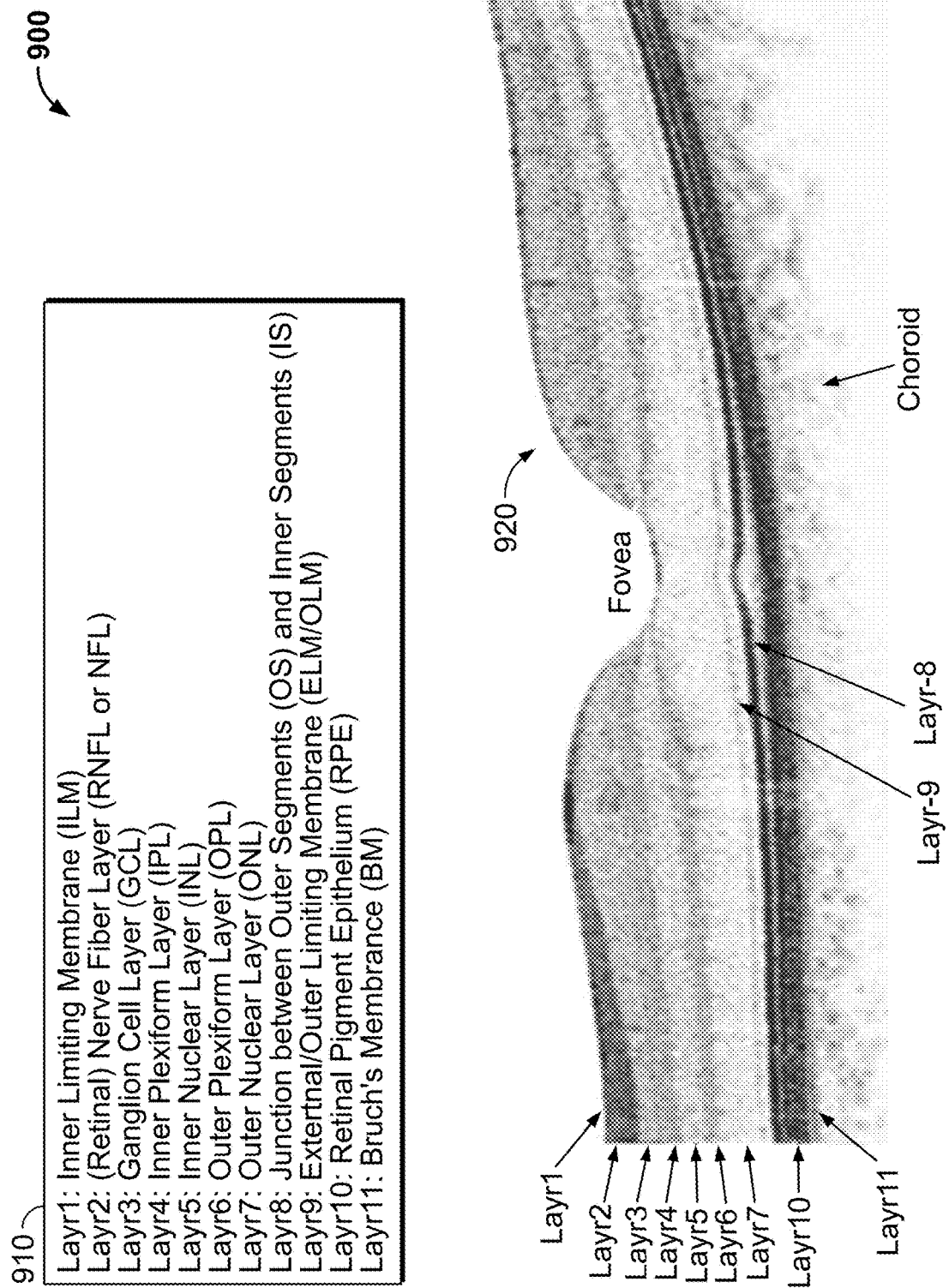

FIG. 9 illustrates an image of an exemplary OCT B-scan image of a normal retina of a human eye and illustratively identifies various canonical retinal layers and boundaries in accordance with various embodiments.

FIG. 10 illustrates an exemplary image of an en-face vasculature image in accordance with various embodiments.

FIG. 11 illustrates an exemplary B-scan of a vasculature (OCTA) image in accordance with various embodiments.

Figure 12:
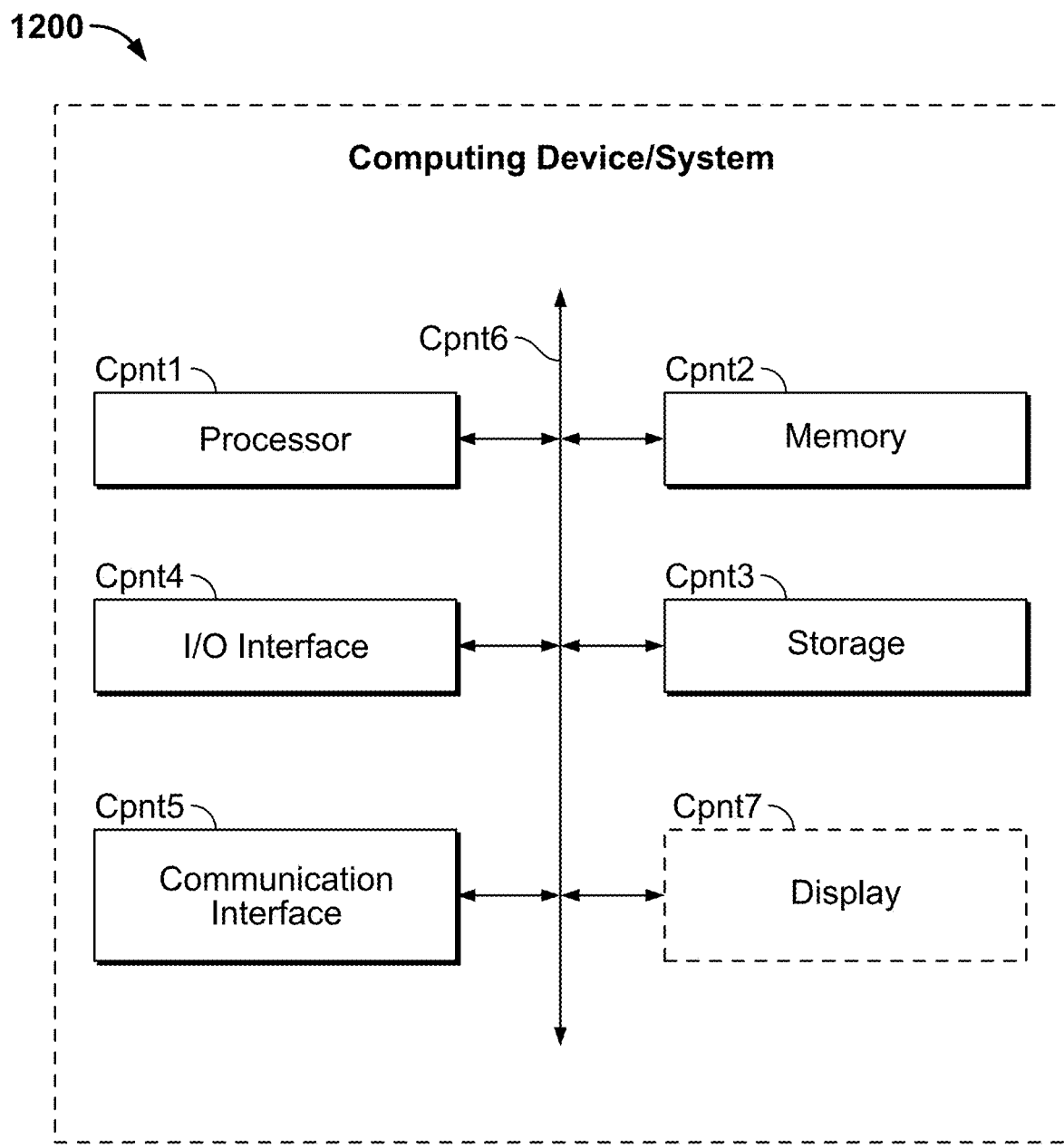

FIG. 12 illustrates a diagram of an example computer system (or computing device or computer) in accordance with various embodiments.

Figure 13:
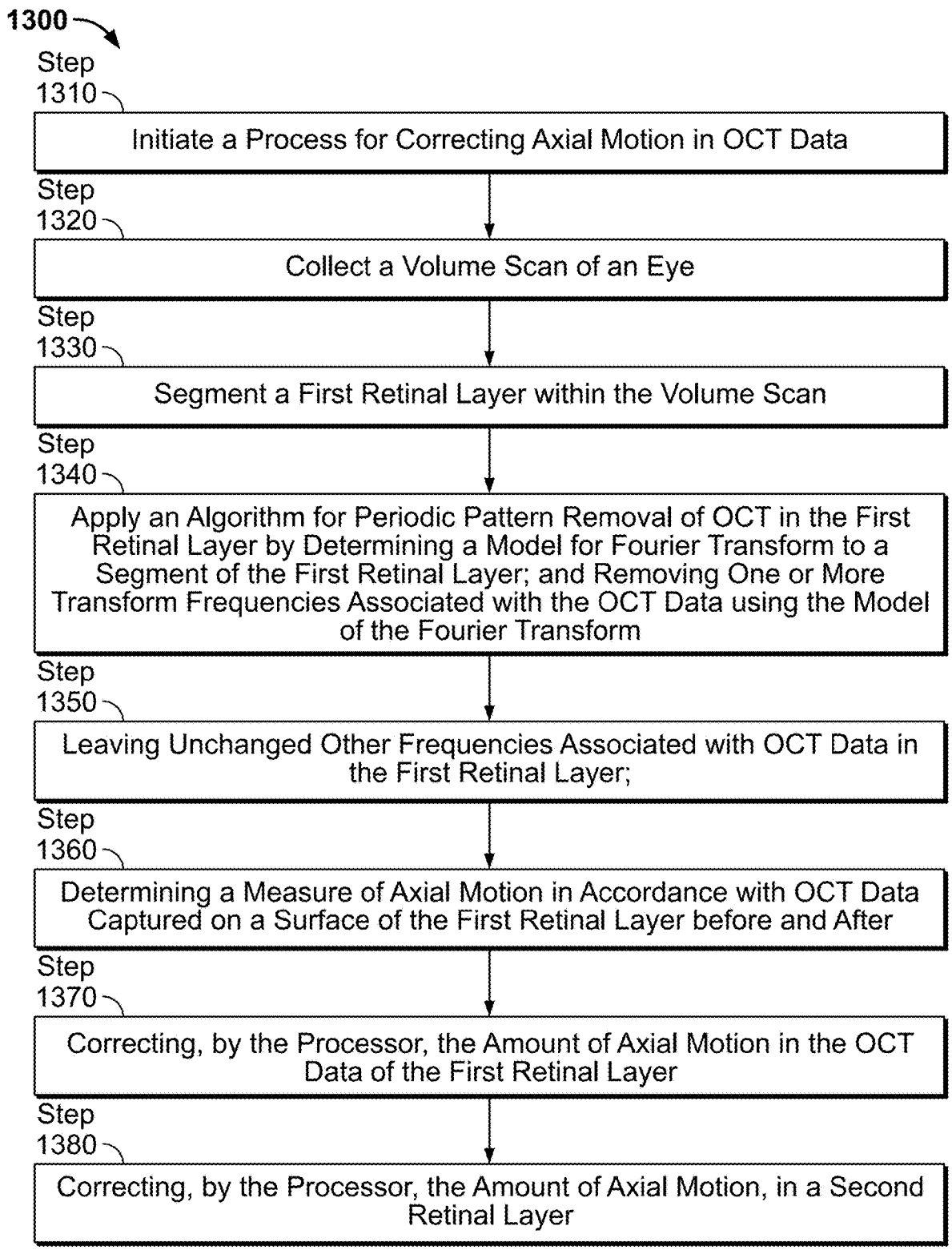

FIG. 13 illustrates an exemplary flowchart of the process for axial motion correction in accordance with various embodiments.

DESCRIPTION OF THE PREFERRED EMBODIMENTS

The following detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that changes may be made without departing from the scope of the disclosure. Thus, the detailed description herein is presented for purposes of illustration only and not for limitation. Furthermore, any reference to singular includes plural embodiments, and any reference to more than one component or step may include a singular embodiment or step. Also, any reference to attached, fixed, connected, or the like may include permanent, removable, temporary, partial, full, or any other possible attachment option. Additionally, any reference to without contact (or similar phrases) may also include reduced contact or minimal contact. It should also be understood that unless specifically stated otherwise, references to "a," "an" or "the" may include one or more than one, and that reference to an item in the singular may also include the item in the plural. Further, all ranges may include upper and lower values, and all ranges and ratio limits disclosed herein may be combined.

When applied to the retina of an eye, OCT imaging displays structural data that, for example, permits one to view distinctive tissue layers and vascular structures of the retina. OCT angiography (OCTA) expands the functionality of an OCT system to also identify (e.g., render in image format) the presence, or lack, of blood flow in retinal tissue. For example, OCTA may identify blood flow by identifying differences over time (e.g., contrast differences) in multiple OCT scans of the same retinal region, and designating differences in the scans that meet predefined criteria as blood flow.

In various implementations, an OCT system may also permit the construction of a planar (2D), frontal view (e.g., enface) image of a select portion of a tissue volume (e.g., a target tissue slab (sub-volume) or target tissue layer(s), such as the retina of an eye). Examples of other 2D representations (e.g., 2D maps) of ophthalmic data provided by an OCT system may include layer thickness maps and retinal curvature maps. For example, to generate layer thickness maps, an OCT system may use en-face images, 2D vasculature maps of the retina, and multilayer segmentation data. Thickness maps may be based, at least in part, on measured thickness differences between retinal layer boundaries. Vasculature maps and OCT enface images may be generated, for example, by projecting onto a 2D surface a sub-volume (e.g., tissue slab) defined between two-layer boundaries. The projection may use the sub-volume mean, sum, percentile, or other data aggregation methods. Thus, the creation of these 2D representations of 3D volume (or sub-volume) data often relies on the effectiveness of automated segmentation algorithms to identify the layers upon which the 2D representations are based.

In various implementations, a motivation for axial motion (Z-motion) correction is to support an analysis that is performed on certain data. Each OCT acquisition takes a finite amount of time, during which the subject is likely to make movements in the axial direction. The axial movement (or other movement) may corrupt the image data, and to compensate for this movement, a correction is necessary. The necessary corrections for Z-motion may also be motivated for aesthetic reasons, or motivated for enhancements in data processing.

For example, the effectiveness of Z-motion correction will affect the accuracy of an automated multi-retinal layer segmentation algorithm. Z-motion correction methods may be based on correlation to a registration scan (e.g., scan data orthogonal to the main scanning direction) that offers some ground truth information regarding the amount of motion. Thus, Z-motion correction depends on the acquisition time of a scan pattern. In other words, Z-motion is more observed if the time difference between two adjacent A-scans along a slow B-scan direction (e.g., perpendicular to a fast B-scan direction) is increased.

The Z-motion correction algorithm may axially shift each of the volume's fast B-scans according to the data in the orthogonal scan. The motion that must be corrected corresponds to forward and backward axial movement. Assuming that the orthogonal scan is motion free and that no lateral motion has occurred during the acquisition, then each A-scan in an orthogonal direction can be correlated to a single A-scan within each fast B-scan of the image.

In implementation the axial motion correction may be challenging due to a number of factors that include: a volume scan that takes an undue amount of time (duration) to complete, especially when a retinal tracking tool is used, and error shifts in raster scans or volume scans that may include X and Y shifts and rotational offsets in the volume data. As a result, the orthogonal scans may not necessarily match exactly to their corresponding slow B-scan in the volume. Also, another impediment in the axial motion correction may be due to low contrast in a subset of A-scans in orthogonal scans that can cause an axial motion correction failure or error. For example, some A-scans can experience low contrast if the A-scans cross the optic nerve head (ONH), large vessels, areas with floaters, etc. Also, obstacles can be caused by X and Y shift errors in volume scans caused by galvo positioning between the B-scans that comprise a volume scan (e.g., during a fly-back operation from the end of a current B-scan in preparation for the start of the next B-scan in the volume scan). Other errors include retinal tracking errors which may cause X and Y shift errors and rotational errors in the volume scan and unmatched orthogonal scans with corresponding slow B-scans caused by large A-scan spacing in the volume.

In various exemplary embodiments, approaches for addressing Z-motion correction are described herein. An approach for axial motion correction of OCT data using multiple pairs of orthogonal scans is described, and an approach for addressing periodic axial motion estimation and correction using low-cost (or lower-quality) OCT data.

Axial Motion Correction of Oct Data Using Multiple Pairs of Orthogonal Scans:

The above problems may be addressed by the use of the following concepts:

Expand the search around a sub-volume around a reference A-scan position in the volume scan for accurate matching.

Select a pair of orthogonal scans from multiple pairs for each B-scan Z-motion estimation and correction. Use the pair of orthogonal scans that leads to the preferred Z-motion correction for a given fast B-scan.

The present embodiment provides for Z-motion correction, including correction due to axial shift and shear (tilt) error, using multiple pairs of orthogonal reference B-scans. This approach overcomes the above-listed limitations due to using a single pair of orthogonal reference B-scans and a limited/small search area for matching A-scans.

In various exemplary embodiments, the present disclosure describes a method and system that uses a small (e.g., limited) number of (optionally freely chosen) sparse orthogonal B-scans for Z-motion correction. In implementation, the search within a sub-volume defined by a reference A-scan position is expanded in the volume scan to achieve a more accurate matching. Multiple (optionally pairs) orthogonal scans are identified as candidate orthogonal scans, and at least one pair of orthogonal scans from the multiple candidate orthogonal scans is selected for each B-scan Z-motion estimation and correction. The pair of orthogonal scans that leads to the preferred Z-motion correction for a given fast B-scan is used/selected. In this way, the present embodiment takes advantage of multiple orthogonal B-scans to estimate the preferred Z-motion correction for each fast B-scan. Also, the search around a sub-volume around the reference A-scan position in the volume scan is expanded for accurate matching.

In various exemplary embodiments, an A-scan can be modeled as a function of space $A(x,y)$ describing the lateral position of the A-scan in an OCT volume. $A(x,y)$ is a d-dimensional vector of intensities equally spaced in the axial direction (z). Let $A_r(x_r, y_r)$ be an orthogonal A-scan at the lateral position r with coordinates $(x_r, y_r)$. The z-motion estimation problem may be formulated as finding the axial motion of each B-scan relative to the reference orthogonal scan data assuming that the orthogonal reference data is motion free (scan time of the scan is very fast and possibly motion free). The $\hat{z}$ position that maximizes an objective function represents the solution and identifies an amount of axial motion in an A-scan of the current B-scan. For instance, the objective function can be the normalized cross-correlation function $\gamma$ between $A(x, y)$ and $A_r(x_r, y_r)$ to find the corresponding $A(x, y)$ of the current B-scan in the orthogonal reference volume, as follows:

$$\hat{z} = \underset{z}{\mathrm{argmax}}(\underset{x,y}{\max}(\gamma(A(x, y), A_r(x_r, y_r), z))$$

The relative shift between $A_r(x_r, y_r)$ and $A(\hat{x}, \hat{y})$ represents the axial shift $\hat{z}$ for one orthogonal scan. The axial shift of two orthogonal scans can be used to compute the B-scan shear (tilt) relative to the reference orthogonal B-scan.

In various embodiments, the Z-motion correction algorithm requires at least a pair of orthogonal B-scans that are taken apart from each other (e.g., at 20% and 80% of the lateral volume position). To improve the performance of the Z-motion correction algorithm, more orthogonal B-scans at different lateral positions may be used. Two consecutive orthogonal B-scans may be considered/grouped as a pair. For instance, five pairs of orthogonal B-scans can be selected from just three pairs of orthogonal B-scans. Basically, 2*N−1 pairs of orthogonal B-scans can be generated from N orthogonal B-scans. For instance, if the three pairs are at positions (10%-90%), (20%-80%), and (30%-70%) of the lateral volume position, then five pairs of consecutive orthogonal B-scans could be defined using positions (10%-90%), (20%-90%), (20%-80%), (30%-80%), and (30%-70%). The Z-motion estimation of the pair (or pairs) of orthogonal B-scans that maximize $\gamma$ is used for the Z-motion correction. This may be an exhaustive search for the preferred Z-motion estimation, which may be computationally expensive. Note that a different pair of A-scans extracted from orthogonal B-scans can be selected for the Z-motion estimation and correction for each fast B-scan.

In various embodiments, a faster or enhanced version of the algorithm may be based on the selection of the orthogonal B-scans. A pair of orthogonal B-scans can be selected based on the quality of the B-scan at each A-scan and the quality of the corresponding slow B-scan and neighboring slow B-scans (e.g., by searching a region). The quality of the B-scans may be measured based on: the axial position of the retina in the orthogonal B-scans; and/or the contrast of the orthogonal B-scans and corresponding slow B-scans including neighboring slow B-scans.

In various embodiments, a method and a system of the present disclosure is directed to correcting axial motion in optical coherence tomography (OCT) data, which includes using an OCT system to access, collect, and/or acquire a volume scan of an eye. A (2D) first retinal layer (e.g., ILM layer) within the volume scan is segmented (extracted) from the volume scan. The first retinal layer is submitted to periodic pattern removal, which may include determining a Fourier transform of the segmented first retinal layer, removing from the Fourier transform frequencies associated with a periodic pattern and leaving other frequencies of the Fourier to transform relatively unchanged, and recovering a cleaned version of the first retinal layer (ILM layer) by taking the inverse Fourier transfer after removal of the frequencies associated with a periodic pattern. The cleaned version of the first retinal layer is then used to define an axial-motion correction map that can be used to correct other layers in the volume. Thus, a measure of axial motion is determined by taking the difference in the surface of the first retinal layer before and after periodic pattern removal. Axial motion in the OCT data is then corrected based on the determined axial motion measure.

In various embodiments, the OCT data whose axial motion is corrected is a second retinal layer, such as the retinal pigment epithelium (RPE) layer. In this case, a retinal thickness map may be defined by taking the difference between the surface of the corrected ILM layer and the corrected RPE layer. The above-mentioned periodic pattern may be identified as being an integral number of oscillations across (e.g., traversing) the Fourier transform.

In various exemplary embodiments, the present disclosure describes methods and systems for correcting axial motion in an optical coherence tomography (OCT) C-scan (volume scan) that include collecting a plurality of pairs of reference scans having a first fast scan direction, and collecting the C-scan, where the C-scan includes multiple B-scans having a second fast scan direction orthogonal to the first fast scan direction. For any select B-scan within the C-scan, a pair of reference scans is dynamically selected from among the plurality of pairs of reference scans. Axial motion correction in the select B-scan is then based on the selected pair of reference scans. The dynamic selection of one pair of reference scans for the select B-scan may include determining a measure of axial motion correction for the select B-scan separately achievable with each pair of reference scans; and defining the pair of reference scans that achieves the preferred measure of axial correction as the dynamically selected one pair of reference scans. In an embodiment of the present invention, where N is the number of reference scans collected, then the number of pairs of reference scans is 2*N−1.

Referring to FIGS. 1A, 1B, and 1C, FIGS. 1A, 1B, and 1C, illustrate a set of multiple scans that comprise three scans with a field-of-view of 6×6 mm, 12×12 mm, and 15×15 mm, respectively, before and after Z-motion correction in accordance with various embodiments. The first (top) row in FIG. 1A shows in the set of B-scans 100 two slow B-scans (5, 10), and the last (bottom) row shows their corresponding two orthogonal B-scans (25, 30). The slow B-scans after correction are shown in the second (middle) row (15, 20). Similar depictions are shown in FIGS. 1B and 1C as follows: FIG. 1B in the set of B-scans 110 there is shown slow B-scans 35, 40; slow B-scans after correction 45, 50; and corresponding two orthogonal scans 55, 60. FIG. 1C in the set of B-scans 120 there is shown slow B-scans 65, 70; slow B-scans after correction 75, 80; and corresponding two orthogonal scans 85, 90.

In an exemplary embodiment, axial motion correction starts by first identifying a reference B-scan in the OCT volume data. The reference B-scan is selected based on the B-scan quality (contrast intensity, and SNR) and central retinal position. Starting with this reference B-scan, the neighboring adjacent B-scans may be registered using normalized cross-correlation in the axial direction. This axial correction is repeated until the entire OCT volume is corrected axially. A CIRRUS™ 6000 AngioPlex (ZEISS, Dublin, CA) was used to image 15 subjects, which was a mix of healthy eyes and diseased eyes, such as aged macular degeneration, macula edema, epiretinal membrane, and diabetic retinopathy. In total, 107 scans were acquired with 12 scans of 3 mm (0.1181 inch)×3 mm (0.1181 inch) and 95 scans of 6 mm (0.2362 inch)×6 mm (0.2362 inch) angiography scans.

In an exemplary embodiment, a grader may review the multi-layer segmentation (MLS) results before and after axial motion correction to evaluate the performance of the axial motion correction. MLS malfunctioned for 31 scans due to the axial motion. After applying the present axial motion correction (AMC), MLS failed only for 1 case out of 107 scans.

Referring to FIGS. 2A and 2B, FIGS. 2A and 2B show examples of the MLS performance before and after axial motion correction. The application of AMC can reduce the failure rate of MLS from approximately 29% to approximately 1%. FIG. 2A illustrates a set of scans and macula thickness map 200 of an example of multilayer segmentation before and after axial motion correction. Central fast scan 205 and slow B-scan 215 and the macular thickness map 225 are also shown before axial motion correction compared to central fast scan 210 and slow B-scan 220 and the macular thickness map 230 after axial motion correction. FIG. 2B is an example scan set 250 of a severe case of multilayer segmentation before and after axial motion correction that comprises central fast scan 255 and slow B-scan 265 and the macular thickness map 275 before axial motion correction compared to central fast scan 260 and slow B-scan 270 and the macular thickness map 280 after axial motion correction.

Periodic Axial Motion Estimation and Correction Using Low-Cost OCT:

As discussed above, motion artifacts in OCT imaging are an important topic in OCT data analysis. Periodic motion artifacts during OCT image acquisition of a patient can be caused by muscular, peristaltic, cardiovascular, respiratory, as well as mechanical vibration in the instrument or any unknown parameters. Degradation of image quality caused by motion can lead to ambiguous clinical interpretations and even erroneous diagnoses.

Retinal Pigment Epithelium (RPE) Elevation Map is one of the advanced diagnostic tools for age-related macular degeneration (AMD) detection and analysis. An RPE elevation map may be used to automatically determine the drusen area and volume. To identify elevations, a 2D surface (RPE fit) is fitted to the RPE segmentation that mimics Bruch's membrane layer. The region between the RPE segmentation and the surface fit defines the RPE elevation.

The requirement for a robust 2D surface fitting to RPE data is a motion artifact-free RPE surface. Motion artifacts can affect the performance of the 2D surface fit.

The typical correction methods for axial/periodic motion are based on correlation to a registration scan (orthogonal scan) that offers some ground truth information regarding the amount of motion. Z-motion depends on the acquisition time of a scan pattern. In other words, axial motion is more observed if the time difference between two adjacent A-scans of a slow B-scan is increased.

While this prior approach typically uses orthogonal B-scans and matches the A-scans of corresponding slow B-scans to the orthogonal B-scans, this requires that reference or registration orthogonal scans must be available for axial motion correct. However, this approach is not suitable for all situations. For example, no orthogonal registration scans may be available in low-cost (e.g., line field) OCT devices due to cost constraints and other technical challenges. Therefore, there is a need for a motion correction method that uses the cube scan data without using any additional registration orthogonal scans.

In various embodiments, the method for periodic motion in OCT data includes RPE segmentation using Fourier transformation (and without the use of orthogonal scans). The repetitive parts of the spectrum associated with the ILM surface are removed by notching out frequencies associated with a periodic pattern and leaving other frequencies of the Fourier to transform relatively unchanged. The difference between the ILM surface before and after periodic pattern removal represents the motion in OCT data in the axial direction. The RPE layer is then corrected using the axial motion data (determined for the ILM surface) prior to RPE fit calculation. This enables a more robust RPE fit calculation.

In an embodiment, the use of reference orthogonal B-scans is not needed nor required; the ILM or any other, segmented layer (e.g., other OCT segmented tissue layer of the eye) can or may be used for axial motion estimation; and the periodic motion is estimated using the Fourier domain.

In an embodiment, the periodic motion may be identified as an integral number of oscillations across the scan, and the axial motion estimation is calculated based on the difference between the ILM surface (or any other designated segmentation boundary layer) before and after periodic pattern removal.

Referring to FIG. 3, FIG. 3 illustrates a flow diagram (process flow) of a process for periodic axial motion correction, that includes images associated with the following nomenclature: ILM=ILM layer boundary surface; ILMcorr=ILM after periodic motion correction; RPE=RPE layer boundary surface; and RPEcorr=RPE after periodic motion correction.

In various exemplary embodiments, the process for correcting for axial motion in OCT data (e.g., a volume scan), begins by collecting/acquiring a volume scan of an eye. A more detailed description of an OCT system acquiring a volume/Cube scan is provided below. A first selected or target retinal layer (or other tissue layers) within the volume scan is then segmented from the volume scan. In the present example, the segmented layer is the ILM layer 311. The segmented retinal layer is then submitted to periodic pattern removal, which in the present example includes determining a Fourier transform of the segmented retinal layer (initial Fourier transform 313). A corrected Fourier transfer may then be defined by removing from the initial Fourier transform 313 frequencies associated with a periodic pattern (e.g., a pattern having an integral number of oscillations across the Fourier transform) and leaving other frequencies of the Fourier transform relatively unchanged. One may then take the inverse Fourier transfer of the corrected Fourier transfer to define a corrected ILM layer (ILMcorr) 315. A measure of the axial motion may then be determined by taking the difference between the surface of the uncorrected ILM layer and the corrected ILM layer, ILMcorr 315. The difference between the ILM surface before 311 and after 315 periodic pattern removal represents the motion in OCT data in the axial direction. This defines an axial-motion correction map 317, and this map 317 can be used to correct the axial motion for each B-scans (in the volume/cube scan) as well as any other retinal layer, such as RPE layer 319. For example, axial motion error in the RPE layer 319 may be corrected by adding the axial-motion correction map 317 to the RPE layer 319 and thereby produce a corrected RPE layer, RPEcorr 321. Thus, axial motion in the initially collected/acquired OCT data is corrected based on the determined axial motion measure, as defined by the axial-motion correction map 317. An accurate retinal thickness map may then be defined by taking the difference between the surface of ILMcorr 315 and RPEcorr 321. In the present example, the ILM layer surface is more suitable for axial motion estimation due to having a higher contrast in OCT data, than some other retina layers, and more successful segmentation. However, other retinal layer surfaces could be used to estimate axial motion.

RPEcorr 321 can then be used for the RPE fit generation which is a 2D surface that mimics Bruch's membrane segmentation. For illustration purposes, FIG. 4 shows in images 400 the difference between RPE fit and RPE before 431 and after 433 axial motion correction.

FIG. 5 shows in the set of images 500 the RPE elevation map 505 generated by setting any value smaller than 20 microns (or other suitable numbers, or normalized values) to zero.

The periodic artifacts can be seen in the difference map (RPE elevation corrected 510) as well as in the RPE elevation map 505 if the axial motion is not compensated prior to the RPE fit generation.

Referring to FIGS. 6A and 6B, FIGS. 6A and 6B provide additional examples of periodic artifacts, with and without correction in accordance with various embodiments. FIG. 6A includes a set of images 600 with and without correction of ILM 605, RPE 610, ILMcorr-ILM 625, RPEcorr-RPE 630, RPEfit-RPE 635, RPE fitcorr-RPE corr 640, RPE elevation 645, and RPE elevation corr 650. FIG. 6B includes a set of images 601 with and without correction of ILM 655, RPE 660, ILMcorr 665, RPEcorr 670, ILMcorr-ILM 675, RPE corr-RPE 680 RPE fit-RPE 685, RPE fitcorr-RPEcorr 690, RPE elevation 695, and RPE elevation corr 699.

Hereinafter is provided a description of various hardware and architectures suitable in accordance with various embodiments.

Referring to FIG. 7, FIG. 7 illustrates an example of a slit scanning ophthalmic system SLO-1 (700) for imaging a fundus F, which is the interior surface of an eye E opposite the eye lens (or crystalline lens) CL and may include the retina, optic disc, macula, fovea, and posterior pole. In the present example, the imaging system is in a so-called "scan-descan" configuration, wherein a scanning line beam SB traverses the optical components of the eye E (including the cornea Cm, iris Irs, pupil Ppl, and crystalline lens CL) to be scanned across the fundus F. In the case of a flood fundus imager, no scanner is needed, and the light is applied across the entire, desired field of view (FOV) at once. Other scanning configurations are known in the art, and the specific scanning configuration is not critical to the present invention. As depicted, the imaging system includes one or more light sources LtSrc, preferably a multi-color LED system or a laser system in which the etendue has been suitably adjusted. An optional slit Slt (adjustable or static) is positioned in front of the light source LtSrc and may be used to adjust the width of the scanning line beam SB. Additionally, slit Slt may remain static during imaging or may be adjusted to different widths to allow for different confocality levels and different applications either for a particular scan or during the scan for use in suppressing reflexes. An optional objective lens ObjL may be placed in front of the slit Slt. The objective lens ObjL can be any one of state-of-the-art lenses including but not limited to refractive, diffractive, reflective, or hybrid lenses/systems. The light from slit Slt passes through a pupil-splitting mirror SM and is directed towards a scanner LnScn. It is desirable to bring the scanning plane and the pupil plane as near together as possible to reduce vignetting in the system. Optional optics DL may be included to manipulate the optical distance between the images of the two components. Pupil splitting mirror SM may pass an illumination beam from light source LtSrc to scanner LnScn, and reflect a detection beam from scanner LnScn (e.g., reflected light returning from eye E) toward a camera Cmr. A task of the pupil-splitting mirror SM is to split the illumination and detection beams and to aid in the suppression of system reflexes. The scanner LnScn could be a rotating galvo scanner or other types of scanners (e.g., piezo or voice coil, micro-electromechanical system (MEMS) scanners, electro-optical deflectors, and/or rotating polygon scanners). Depending on whether the pupil splitting is done before or after the scanner LnScn, the scanning could be broken into two steps wherein one scanner is in an illumination path and a separate scanner is in a detection path. Specific pupil splitting arrangements are described in detail in U.S. Pat. No. 9,456,746, which is herein incorporated in its entirety by reference.

From the scanner LnScn, the illumination beam passes through one or more optics, in this case, a scanning lens SL and an ophthalmic or ocular lens OL, that allow for the pupil of the eye E to be imaged to an image pupil of the system. Generally, the scan lens SL receives a scanning illumination beam from the scanner LnScn at any of multiple scan angles (incident angles) and produces a scanning line beam SB with a substantially flat surface focal plane (e.g., a collimated light path). Ophthalmic lens OL may then focus the scanning line beam SB onto an object to be imaged. In the present example, the ophthalmic lens OL focuses the scanning line beam SB onto the fundus F (or retina) of eye E to image the fundus. In this manner, scanning line beam SB creates a traversing scan line that travels across the fundus F. One possible configuration for these optics is a Kepler-type telescope wherein the distance between the two lenses is selected to create an approximately telecentric intermediate fundus image (4-f configuration). The ophthalmic lens OL could be a single lens, an achromatic lens, or an arrangement of different lenses. All lenses could be refractive, diffractive, reflective, or hybrid as known to one skilled in the art. The focal length(s) of the ophthalmic lens OL, scan lens SL, and the size and/or form of the pupil splitting mirror SM and scanner LnScn could be different depending on the desired field of view (FOV), and so an arrangement in which multiple components can be switched in and out of the beam path, for example by using a flip in optic, a motorized wheel, or a detachable optical element, depending on the field of view can be envisioned. Since the field of view change results in a different beam size on the pupil, the pupil splitting can also be changed in conjunction with the change to the FOV. For example, a 45° to 60° field of view is a typical, or standard, FOV for fundus cameras. Higher fields of view, e.g., a widefield FOV, of 60°-120°, or more, may also be feasible. A widefield FOV may be desired for a combination of the Broad-Line Fundus Imager (BLFI) with other imaging modalities such as optical coherence tomography (OCT). The upper limit for the field of view may be determined by the accessible working distance in combination with the physiological conditions around the human eye. Because a typical human retina has a FOV of 140° horizontal and 80°-100° vertical, it may be desirable to have an asymmetrical field of view for the highest possible FOV on the system.

The scanning line beam SB passes through the pupil Ppl of the eye E and is directed towards the retinal, or fundus, surface F. The scanner LnScn1 adjusts the location of the light on the retina, or fundus, F such that a range of transverse locations on the eye E is illuminated. Reflected or scattered light (or emitted light in the case of fluorescence imaging) is directed back along a similar path as the illumination to define a collection beam CB on a detection path to camera Cmr.

In the "scan-descan" configuration of the present, exemplary slit scanning ophthalmic system SLO-1, light returning from the eye E is "descanned" by scanner LnScn on its way to pupil splitting mirror SM. That is, scanner LnScn scans the illumination beam from pupil splitting mirror SM to define the scanning illumination beam SB across eye E, but since scanner LnScn also receives returning light from eye E at the same scan position, scanner LnScn has the effect of descanning the returning light (e.g., canceling the scanning action) to define a non-scanning (e.g., steady or stationary) collection beam from scanner LnScn to pupil splitting mirror SM, which folds the collection beam toward camera Cmr. At the pupil splitting mirror SM, the reflected light (or emitted light in the case of fluorescence imaging) is separated from the illumination light onto the detection path directed towards camera Cmr, which may be a digital camera having a photo sensor to capture an image. An imaging (e.g., objective) lens ImgL may be positioned in the detection path to image the fundus to the camera Cmr. As is the case for objective lens ObjL, imaging lens ImgL may be any type of lens known in the art (e.g., refractive, diffractive, reflective, or hybrid lens). Additional operational details, in particular, ways to reduce artifacts in images, are described in PCT Publication No. WO2016/124644, the contents of which are herein incorporated in their entirety by reference. The camera Cmr captures the received image, e.g., it creates an image file, which can be further processed by one or more (electronic) processors or computing devices (e.g., the computer system of FIG. 12). Thus, the collection beam (returning from all scan positions of the scanning line beam SB) is collected by the camera Cmr, and a full-frame image Img may be constructed from a composite of the individually captured collection beams, such as by montaging. However, other scanning configurations are also contemplated, including ones where the illumination beam is scanned across the eye E and the collection beam is scanned across a photosensor array of the camera. PCT Publication WO 2012/059236 and US Patent Publication No. 2015/0131050, herein incorporated by reference, describe several embodiments of slit scanning ophthalmoscopes including various designs where the returning light is swept across the camera's photo sensor array and where the returning light is not swept across the camera's photo sensor array.

In the present example, the camera Cmr is connected to a processor (e.g., processing module) Proc and a display (e.g., displaying module, computer screen, electronic screen, etc.) Dspl, both of which can be part of the imaging system itself, or maybe part of separate, dedicated processing and/or displaying unit(s), such as a computer system wherein data is passed from the camera Cmr to the computer system over a cable or computer network including wireless networks. The display and processor can be an all-in-one unit. The display can be a traditional electronic display/screen or of the touch screen type and can include a user interface for displaying information to and receiving information from an instrument operator or user. The user can interact with the display using any type of user input device as known in the art including, but not limited to, a mouse, knobs, buttons, pointer, and touch screen.

It may be desirable for a patient's gaze to remain fixed while imaging is carried out. One way to achieve this is to provide a fixation target that the patient can be directed to stare at. Fixation targets can be internal or external to the instrument depending on what area of the eye is to be imaged. One embodiment of an internal fixation target is shown in FIG. 7. In addition to the primary light source LtSrc used for imaging, a second optional light source FxLtSrc, such as one or more LEDs, can be positioned such that a light pattern is imaged to the retina using lens FxL, scanning element FxScn and reflector/mirror FxM. Fixation scanner FxScn can move the position of the light pattern and reflector FxM directs the light pattern from fixation scanner FxScn to the fundus F of eye E. Preferably, fixation scanner FxScn is positioned such that it is located at the pupil plane of the system so that the light pattern on the retina/fundus can be moved depending on the desired fixation location.

Slit-scanning ophthalmoscope systems are capable of operating in different imaging modes depending on the light source and wavelength-selective filtering elements employed. True color reflectance imaging (imaging similar to that observed by the clinician when examining the eye using a hand-held or slit lamp ophthalmoscope) can be achieved when imaging the eye with a sequence of colored LEDs (red, blue, and green). Images of each color can be built up in steps with each LED turned on at each scanning position or each color image can be taken in its entirety separately. The three, color images can be combined to display the true color image, or they can be displayed individually to highlight different features of the retina. The red channel preferred highlights the choroid, the green channel highlights the retina, and the blue channel highlights the anterior retinal layers. Additionally, the light at specific frequencies (e.g., individual-colored LEDs or lasers) can be used to excite different fluorophores in the eye (e.g., autofluorescence) and the resulting fluorescence can be detected by filtering out the excitation wavelength.

The fundus imaging system can also provide an infrared reflectance image, such as by using an infrared laser (or other infrared light sources). The infrared (IR) mode is advantageous in that the eye is not sensitive to the IR wavelengths. This may permit a user to continuously take images without disturbing the eye (e.g., in a preview/alignment mode) to aid the user during the alignment of the instrument. Also, the IR wavelengths have increased penetration through tissue and may provide improved visualization of choroidal structures. In addition, fluorescein angiography (FA) and indocyanine green (ICG) angiography imaging can be accomplished by collecting images after a fluorescent dye has been injected into the subject's bloodstream. For example, in FA (and/or ICG) a series of time-lapse images may be captured after injecting a light-reactive dye (e.g., fluorescent dye) into a subject's bloodstream. It is noted that care must be taken since the fluorescent dye may lead to a life-threatening allergic reaction in a portion of the population. High contrast, greyscale images are captured using specific light frequencies selected to excite the dye. As the dye flows through the eye, various portions of the eye are made to glow brightly (e.g., fluoresce), making it possible to discern the progress of the dye, and hence the blood flow, through the eye.

Optical Coherence Tomography Imaging System

Generally, optical coherence tomography (OCT) uses low-coherence light to produce two-dimensional (2D) and three-dimensional (3D) internal views of biological tissue. OCT enables in vivo imaging of retinal structures. OCT angiography (OCTA) produces flow information, such as vascular flow from within the retina. Examples of OCT systems are provided in U.S. Pat. Nos. 6,741,359 and 9,706,915, and examples of an OCTA system may be found in U.S. Pat. Nos. 9,700,206 and 9,759,544, all of which are herein incorporated in their entirety by reference. An exemplary OCT/OCTA system is provided herein.

Referring to FIG. 8, FIG. 8 illustrates a generalized frequency domain optical coherence tomography (FD-OCT) system 800 used to collect 3D image data of the eye suitable for use in accordance with various embodiments. An FD-OCT system OCT_1 includes a light source, LtSrc1. Typical light sources include but are not limited to, broadband light sources with short temporal coherence lengths or swept laser sources. A beam of light from light source LtSrc1 is routed, typically by optical fiber Fbr1, to illuminate a sample, e.g., eye E; a typical sample being tissues in the human eye. The light source LrSrc1 may, for example, be a broadband light source with short temporal coherence length in the case of spectral domain OCT (SD-OCT) or a wavelength tunable laser source in the case of swept source OCT (SS-OCT). The light may be scanned, typically with a scanner Scnr1 between the output of the optical fiber Fbr1 and the sample E, so that the beam of light (dashed line Bm) is scanned laterally over the region of the sample to be imaged. The light beam from scanner Scnr1 may pass through a scan lens SL and an ophthalmic lens OL and be focused onto the sample E being imaged. The scan lens SL may receive the beam of light from the scanner Scnr1 at multiple incident angles and produce substantially collimated light, and the ophthalmic lens OL may then focus onto the sample. The present example illustrates a scan beam that needs to be scanned in two lateral directions (e.g., in x and y directions on a Cartesian plane) to scan a desired field of view (FOV). An example of this would be a point-field OCT, which uses a point-field beam to scan across a sample. Consequently, scanner Scnr1 is illustratively shown to include two sub-scanner: a first sub-scanner Xscn for scanning the point-field beam across the sample in a first direction (e.g., a horizontal x-direction); and a second sub-scanner Yscn for scanning the point-field beam on the sample in traversing second direction (e.g., a vertical y-direction). If the scan beam were a line-field beam (e.g., a line-field OCT), which may sample an entire line portion of the sample at a time, then only one scanner may be needed to scan the line-field beam across the sample to span the desired FOV. If the scan beam were a full-field beam (e.g., a full-field OCT), no scanner may be needed, and the full-field light beam may be applied across the entire, desired FOV at once.

Irrespective of the type of beam used, light scattered from the sample (e.g., sample light) is collected. In the present example, scattered light returning from the sample is collected into the same optical fiber Fbr1 used to route the light for illumination. Reference light derived from the same light source LtSrc1 travels a separate path, in this case involving optical fiber Fbr2 and retro-reflector RR1 with an adjustable optical delay. Those skilled in the art will recognize that a transmissive reference path can also be used and that the adjustable delay could be placed in the sample or reference arm of the interferometer. Collected sample light is combined with reference light, for example, in a fiber coupler Cplr1, to form light interference in an OCT light detector Dtctr1 (e.g., photodetector array, digital camera, etc.). Although a single fiber port is shown going to the detector Dtctr1, those skilled in the art will recognize that various designs of interferometers can be used for balanced or unbalanced detection of the interference signal. The output from the detector Dtctr1 is supplied to a processor (e.g., internal or external computing device) Cmp1 that converts the observed interference into depth information of the sample. The depth information may be stored in a memory associated with the processor Cmp1 and/or displayed on a display (e.g., computer/electronic display/screen) Scn1. The processing and storing functions may be localized within the OCT instrument, or functions may be offloaded onto (e.g., performed on) an external processor (e.g., an external computing device), to which the collected data may be transferred. An example of a computing device (or computer system) is shown in FIG. 12. This unit could be dedicated to data processing or perform other tasks which are quite general and not dedicated to the OCT device. The processor (computing device) Cmp1 may include, for example, a field-programmable gate array (FPGA), a digital signal processor (DSP), an application-specific integrated circuit (ASIC), a graphics processing unit (GPU), a system-on-chip (SoC), a central processing unit (CPU), a general purpose graphics processing unit (GPGPU), or a combination thereof, that may perform some, or the entire, processing steps in a serial and/or parallelized fashion with one or more host processors and/or one or more external computing devices.

The sample and reference arms in the interferometer could consist of bulk-optics, fiber-optics, or hybrid bulk-optic systems and could have different architectures such as Michelson, Mach-Zehnder, or common-path-based designs as would be known by those skilled in the art. Light beam as used herein should be interpreted as any carefully directed light path. Instead of mechanically scanning the beam, a field of light can illuminate a one or two-dimensional area of the retina to generate the OCT data (see, for example, U.S. Pat. No. 9,332,902; D. Hillmann et al, "Holoscopy—Holographic Optical Coherence Tomography," *Optics Letters*, 36(13): 2390 2011; Y. Nakamura, et al, "High-Speed Three Dimensional Human Retinal Imaging by Line Field Spectral Domain Optical Coherence Tomography," *Optics Express*, 15(12):7103 2007; Blazkiewicz et al, "Signal-To-Noise Ratio Study of Full-Field Fourier-Domain Optical Coherence Tomography," *Applied Optics*, 44(36):7722 (2005)). In time-domain systems, the reference arm needs to have a tunable optical delay to generate interference. Balanced detection systems are typically used in TD-OCT and SS-OCT systems, while spectrometers are used at the detection port for SD-OCT systems. The invention described herein could be applied to any type of OCT system. Various aspects of the invention could apply to any type of OCT system or other types of ophthalmic diagnostic systems and/or multiple ophthalmic diagnostic systems including but not limited to fundus imaging systems, visual field test devices, and scanning laser polarimeters.

In Fourier Domain optical coherence tomography (FD-OCT), each measurement is the real-valued spectral interferogram (Sj(k)). The real-valued spectral data typically goes through several post-processing steps including background subtraction, dispersion correction, etc. The Fourier transform of the processed interferogram results in a complex-valued OCT signal output $Aj(z)=|Aj|e^{i\varphi}$. The absolute value of this complex OCT signal, $|Aj|$, reveals the profile of scattering intensities at different path lengths, and therefore scattering as a function of depth (z-direction) in the sample. Similarly, the phase, $\varphi j$ can also be extracted from the complex-valued OCT signal. The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube. For a particular volume of data, the term fast axis refers to the scan direction along a single B-scan whereas the slow axis refers to the axis along which multiple B-scans are collected. The term "cluster scan" may refer to a single unit or block of data generated by repeated acquisitions at the same (or substantially the same) location (or region) for the purposes of analyzing motion contrast, which may be used to identify blood flow. A cluster scan can consist of multiple A-scans or B-scans collected with relatively short time separations at approximately the same location(s) on the sample. Since the scans in a cluster scan are of the same region, static structures remain relatively unchanged from scan to scan within the cluster scan, whereas motion contrast between the scans that meet predefined criteria may be identified as blood flow.

A variety of ways to create B-scans are known in the art including but not limited to: along the horizontal or x-direction, along the vertical or y-direction, along the diagonal of x and y, or in a circular or spiral pattern. B-scans may be in the x-z dimensions but may be any cross-sectional image that includes the z-dimension. An example OCT B-scan image 920 of a normal retina of a human eye is illustrated in FIG. 9. An OCT B-scan 900 of the retina provides a view of the structure of retinal tissue. For illustration purposes, FIG. 9 identifies various canonical retinal layers and layer boundaries. The identified retinal boundary layers 910 include (from top to bottom): the inner limiting membrane (ILM) Lyer1, the retinal nerve fiber layer (RNFL or NFL) Layr2, the ganglion cell layer (GCL) Layr3, the inner plexiform layer (IPL) Layr4, the inner nuclear layer (INL) Layr5, the outer plexiform layer (OPL) Layr6, the outer nuclear layer (ONL) Layr7, the junction between the outer segments (OS) and inner segments (IS) (indicated by reference character Layr8) of the photoreceptors, the external or outer limiting membrane (ELM or OLM) Layr9, the retinal pigment epithelium (RPE) Layr10, and the Bruch's membrane (BM) Layr11.

In OCT Angiography, or Functional OCT, analysis algorithms may be applied to OCT data collected at the same, or approximately the same, sample locations on a sample at different times (e.g., a cluster scan) to analyze motion or flow (see for example US Patent Publication Nos. 2005/0171438, 2012/0307014, 2010/0027857, 2012/0277579 and U.S. Pat. No. 6,549,801, all of which are herein incorporated in their entirety by reference). An OCT system may use any one of a number of OCT angiography processing algorithms (e.g., motion contrast algorithms) to identify blood flow. For example, motion contrast algorithms can be applied to the intensity information derived from the image data (intensity-based algorithm), the phase information from the image data (phase-based algorithm), or the complex image data (complex-based algorithm). An en face image is a 2D projection of 3D OCT data (e.g., by averaging the intensity of each individual A-scan, such that each A-scan defines a pixel in the 2D projection). Similarly, an en-face vasculature image is an image displaying a motion contrast signal in which the data dimension corresponding to depth (e.g., z-direction along an A-scan) is displayed as a single representative value (e.g., a pixel in a 2D projection image), typically by summing or integrating all or an isolated portion of the data (see for example U.S. Pat. No. 7,301,644 herein incorporated in its entirety by reference). OCT systems that provide an angiography imaging functionality may be termed OCT angiography (OCTA) systems.

Referring to FIG. 10, FIG. 10 shows an example of an en-face vasculature image 1010. After processing the data to highlight motion contrast using any of the motion contrast techniques known in the art, a range of pixels corresponding to a given tissue depth from the surface of the internal limiting membrane (ILM) in the retina, may be summed to generate the en face (e.g., frontal view) image of the vasculature. Referring to FIG. 11, FIG. 11 shows an exemplary B-scan of a vasculature (OCTA) image 1100. As illustrated, structural information may not be well-defined since blood flow may traverse multiple retinal layers making them less defined than in a structural OCT B-scan, as shown in FIG. 9. Nonetheless, OCTA provides a non-invasive technique for imaging the microvasculature of the retina and the choroid, which may be critical to diagnosing and/or monitoring various pathologies. For example, OCTA may be used to identify diabetic retinopathy by identifying microaneurysms, and neovascular complexes, and quantifying foveal avascular zone and nonperfused areas. Moreover, OCTA has been shown to be in good agreement with fluorescein angiography (FA), a more traditional, but evasive, technique requiring the injection of a dye to observe vascular flow in the retina. Additionally, in dry age-related macular degeneration, OCTA has been used to monitor a general decrease in choriocapillaris flow. Similarly, in wet age-related macular degeneration, OCTA can provide a qualitative and quantitative analysis of choroidal neovascular membranes. OCTA has also been used to study vascular occlusions, e.g., evaluation of nonperfused areas and the integrity of superficial and deep plexus.

Computing Device/System

Referring to FIG. 12, FIG. 12 illustrates an example computer system (or computing device or computer device) 1200. In some embodiments, one or more computer systems may provide the functionality described or illustrated herein and/or perform one or more steps of one or more methods described or illustrated herein. The computer system may take any suitable physical form. For example, the computer system may be an embedded computer system, a system-on-chip (SOC), a single-board computer system (SBC) (such as, for example, a computer-on-module (COM) or system-on-module (SOM)), a desktop computer system, a laptop or notebook computer system, a mesh of computer systems, a mobile telephone, a personal digital assistant (PDA), a server, a tablet computer system, an augmented/virtual reality device, or a combination of two or more of these. Where appropriate, the computer system may reside in a cloud, which may include one or more cloud components in one or more networks.

In some embodiments, the computer system may include a processor Cpnt1, memory Cpnt2, storage Cpnt3, an input/output (I/O) interface Cpnt4, a communication interface Cpnt5, and a bus Cpnt6. The computer system may optionally also include a display Cpnt7, such as a computer monitor or screen.

Processor Cpnt1 includes hardware for executing instructions, such as those making up a computer program. For example, processor Cpnt1 may be a central processing unit (CPU) or a general-purpose computing on the graphics processing unit (GPGPU). Processor Cpnt1 may retrieve (or fetch) the instructions from an internal register, an internal cache, memory Cpnt2, or storage Cpnt3, decode and execute the instructions, and write one or more results to an internal register, an internal cache, memory Cpnt2, or storage Cpnt3. In particular embodiments, processor Cpnt1 may include one or more internal caches for data, instructions, or addresses. Processor Cpnt1 may include one or more instruction caches, and one or more data caches, such as to hold data tables. Instructions in the instruction caches may be copies of instructions in memory Cpnt2 or storage Cpnt3, and the instruction caches may speed up retrieval of those instructions by processor Cpnt1. Processor Cpnt1 may include any suitable number of internal registers and may include one or more arithmetic logic units (ALUs). Processor Cpnt1 may be a multi-core processor or include one or more processors Cpnt1. Although this disclosure describes and illustrates a particular processor, this disclosure contemplates any suitable processor.

Memory Cpnt2 may include main memory for storing instructions for processor Cpnt1 to execute or to hold interim data during processing. For example, the computer system may load instructions or data (e.g., data tables) from storage Cpnt3 or from another source (such as another computer system) to memory Cpnt2. Processor Cpnt1 may load the instructions and data from memory Cpnt2 to one or more internal registers or internal cache. To execute the instructions, processor Cpnt1 may retrieve and decode the instructions from the internal register or internal cache. During or after execution of the instructions, processor Cpnt1 may write one or more results (which may be intermediate or final results) to the internal register, internal cache, memory Cpnt2, or storage Cpnt3. Bus Cpnt6 may include one or more memory buses (which may each include an address bus and a data bus) and may couple processor Cpnt1 to memory Cpnt2 and/or storage Cpnt3. Optionally, one or more memory management units (MMU) facilitate data transfers between processor Cpnt1 and memory Cpnt2. Memory Cpnt2 (which may be fast, volatile memory) may include random access memory (RAM), such as dynamic RAM (DRAM) or static RAM (SRAM). Storage Cpnt3 may include long-term or mass storage for data or instructions. Storage Cpnt3 may be internal or external to the computer system, and include one or more of a disk drive (e.g., hard-disk drive, HDD, or solid-state drive, SSD), flash memory, ROM, EPROM, optical disc, a magneto-optical disc, magnetic tape, Universal Serial Bus (USB)-accessible drive, or other types of non-volatile memory.

I/O interface Cpnt4 may be software, hardware, or a combination of both, and include one or more interfaces (e.g., serial or parallel communication ports) for communication with I/O devices, which may enable communication with a person (e.g., user). For example, I/O devices may include a keyboard, keypad, microphone, monitor, mouse, printer, scanner, speaker, still camera, stylus, tablet, touch screen, trackball, video camera, another suitable I/O device, or a combination of two or more of these.

Communication interface Cpnt5 may provide network interfaces for communication with other systems or networks. Communication interface Cpnt5 may include a Bluetooth interface or other types of packet-based communication. For example, communication interface Cpnt5 may include a network interface controller (NIC) and/or a wireless NIC or a wireless adapter for communicating with a wireless network. Communication interface Cpnt5 may provide communication with a WI-FI network, an ad hoc network, a personal area network (PAN), a wireless PAN (e.g., a Bluetooth WPAN), a local area network (LAN), a wide area network (WAN), a metropolitan area network (MAN), a cellular telephone network (such as, for example, a Global System for Mobile Communications (GSM) network), the Internet, or a combination of two or more of these.

Bus Cpnt6 may provide a communication link between the above-mentioned components of the computing system. For example, bus Cpnt6 may include an Accelerated Graphics Port (AGP) or other graphics bus, an Enhanced Industry Standard Architecture (EISA) bus, a front-side bus (FSB), a HyperTransport (HT) interconnect, an Industry Standard Architecture (ISA) bus, an InfiniBand bus, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or other suitable bus or a combination of two or more of these.

Although this disclosure describes and illustrates a particular computer system having a particular number of particular components in a particular arrangement, this disclosure contemplates any suitable computer system having any suitable number of any suitable components in any suitable arrangement.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Referring to FIG. 13, FIG. 13 illustrates a flowchart 1300 of the axial motion correction process in accordance with various embodiments. In FIG. 13, at step 1310, a computing device (i.e., processor) operably disposed in an OCT device is initiated to cause a compensation or correction of axial motion in a B-scan (or other scan type). At step 1320, the computing device collects a volume scan of an eye. At step 1330, the computing device is programmed with algorithm or implements a software application that segments a first retinal layer within the volume scan. At step 1340, the computing device applies an algorithm that enables periodic pattern removal of OCT data in the first retinal layer. The periodic pattern removal of the OCT data is performed by determining a model of a Fourier transform applicable to a segment of the first retinal layer; and removing one or more transform frequencies associated with the OCT data using the model of the Fourier transform for the periodic pattern removal. At step 1350, the process of removal of the periodic pattern is performed while leaving unchanged other frequencies associated with OCT data in the first retinal layer. At step 1360, the computing device is programmed to determine a measure of an amount of axial motion in accordance with a difference in an amount of OCT data captured on a surface of the first retinal layer before and after application of the algorithm for periodic pattern removal. At step 1370, the computing device is programmed to correct the amount of axial motion in the OCT data of the first retinal layer. At step 1380, the computing device is to repeat the process flow for a second retinal layer and to correct the amount of axial motion in the scan of the second retinal layer. In this manner, multiple layers in the retina are corrected for axial motion that enhances the image generated by the OCT data.

While the invention has been described in conjunction with several specific embodiments, it is evident to those skilled in the art that many further alternatives, modifications, and variations will be apparent in light of the foregoing description. Thus, the invention described herein is intended to embrace all such alternatives, modifications, applications, and variations as may fall within the spirit and scope of the appended claims.

What is claimed:

1. A method for correcting for axial motion in optical coherence tomography (OCT) data, comprising:
   collecting, by a processor disposed of in an OCT device, a volume scan of an eye;
   segmenting, by the processor, a first retinal layer within the volume scan;
   applying, by the processor, an algorithm for periodic pattern removal of OCT data in the first retinal layer by:
      determining a model of a Fourier transform applicable to a segment of the first retinal layer; and
      removing one or more transform frequencies associated with the OCT data using the model of the Fourier transform for the periodic pattern removal while leaving unchanged other frequencies associated with OCT data in the first retinal layer;
   determining, by the processor, a measure of an amount of axial motion in accordance with a difference in an amount of OCT data captured on a surface of the first retinal layer before and after application of the algorithm for periodic pattern removal; and
   correcting, by the processor, the amount of axial motion in the OCT data of the first retinal layer.

2. The method of claim 1, wherein the periodic pattern removal further comprises recovering by the processor of a motion-corrected version of the first retinal layer by applying an inverse Fourier transfer after removal of the frequencies associated with the periodic pattern removal.

3. The method of claim 1, further comprising:
   correcting, by the processor, the amount of axial motion, in a second retinal layer.

4. The method of claim 3, wherein the first retina layer comprises an internal limiting membrane (ILM) layer, and the second retinal layer comprises retinal pigment epithelium (RPE) layer.

5. The method of claim 1, further comprising: defining, by the processor, a retinal thickness map in accordance with a difference in the amount of OCT data contained on the surface of the ILM layer and the RPE layer after application of an axial motion correction to the ILM layer and the RPE layer.

6. The method of claim 1, wherein the model for periodic pattern removal is determined by an integral number of oscillations across the Fourier transform.

7. The method of claim 1, wherein the first retinal layer at least comprises a two-dimensional retinal layer.

8. A system for correcting axial motion error in optical coherence tomography (OCT) data, comprising:
   an OCT device configured to collect a volume scan of an eye; and
   a processor disposed of in the OCT device configured to:
      apply an algorithm for periodic pattern removal of OCT data in a first retinal layer to:
         determine a model of a Fourier transform applicable to a segment of the first retinal layer; and
         remove one or more transform frequencies associated with the OCT data using the model of the Fourier transform for the periodic pattern removal while leaving unchanged other frequencies associated with OCT data in the first retinal layer;
      determine a measure of an amount of axial motion in accordance with a difference in an amount of OCT data captured on a surface of the first retinal layer before and after application of the algorithm for periodic pattern removal; and
      correct the amount of axial motion in the OCT data of the first retinal layer.

9. The system of claim 8, wherein the processor is configured to: correct the amount of axial motion in a second retinal layer.

10. The system of claim 9, wherein the first retinal layer is positioned higher than the second retinal layer within a retina of the eye.

11. The system of claim 10, wherein the first retinal layer comprises an internal limiting membrane (ILM) layer, and the second retinal layer comprises a retinal pigment epithelium (RPE) layer.

12. The system of claim 11, wherein the processor is configured to define a retinal thickness map in accordance with a difference in the amount of OCT data contained on the surface of the ILM layer and the RPE layer after application of an axial motion correction to the ILM layer and the RPE layer.

13. The system of claim 12, wherein the model for periodic pattern removal is determined by an integral number of oscillations across the Fourier transform.

14. The system of claim 13, wherein the first retinal layer at least comprises a two-dimensional retinal layer.

* * * * *